US006944322B2

(12) United States Patent
Johnson et al.

(10) Patent No.: US 6,944,322 B2
(45) Date of Patent: Sep. 13, 2005

(54) OPTICAL TOMOGRAPHY OF SMALL OBJECTS USING PARALLEL RAY ILLUMINATION AND POST-SPECIMEN OPTICAL MAGNIFICATION

(75) Inventors: Roger H. Johnson, Whitefish Bay, WI (US); Alan C. Nelson, Gig Harbor, WA (US)

(73) Assignee: VisionGate, Inc., Gig Harbor, WA (US)

( * ) Notice: Subject to any disclaimer, the term of this patent is extended or adjusted under 35 U.S.C. 154(b) by 0 days.

(21) Appl. No.: 10/308,309

(22) Filed: Dec. 3, 2002

(65) Prior Publication Data

US 2004/0001618 A1 Jan. 1, 2004

Related U.S. Application Data

(63) Continuation-in-part of application No. 09/927,151, filed on Aug. 10, 2001, now Pat. No. 6,522,775.
(60) Provisional application No. 60/279,244, filed on Mar. 28, 2001.

(51) Int. Cl.[7] .............................................. G06K 9/00
(52) U.S. Cl. ...................................................... 382/128
(58) Field of Search ................................. 382/120, 129, 382/131, 133; 435/448; 600/309, 310; 378/6, 7, 8, 44, 45, 49, 50; 430/8, 21, 139, 503, 508, 511; 702/19, 21, 28

(56) References Cited

U.S. PATENT DOCUMENTS

| | | |
|---|---|---|
| 3,470,373 A | 9/1969 | Brewer .................... 250/461.2 |
| 3,497,690 A | 2/1970 | Wheeless, Jr. ............ 250/461.2 |
| 3,598,471 A | 8/1971 | Baldwin .................... 359/562 |
| 3,657,537 A | 4/1972 | Wheeless, Jr. ............ 250/461.2 |
| 3,748,468 A | 7/1973 | Hartman .................... 250/311 |
| 3,833,762 A | 9/1974 | Gudmundsen .......... 348/208.99 |
| 3,960,449 A | 6/1976 | Carlton .................... 356/340 |
| 3,999,047 A | 12/1976 | Green ..................... 382/134 |
| 4,175,860 A | 11/1979 | Bacus ...................... 356/39 |
| 4,200,353 A | 4/1980 | Hoffman .................. 359/370 |

(Continued)

FOREIGN PATENT DOCUMENTS

WO    WO 02/095476 A2    11/2002    ........... G02B/21/26

OTHER PUBLICATIONS

Sharpe, J, Ahlgren, U et al., "Optical Projection Tomography as a Tool for 3D Microscopy and Gene Expression Studies," SCIENCE, vol. 296, pp. 541–545, Apr. 19, 2002.
Sharpe, J, review, "Optical Projection Tomography as a New Tool for Studying Embryo Anatomy," *J. Anat.* (2003), pp. 175–181.

(Continued)

*Primary Examiner*—Andrew W. Johns
*Assistant Examiner*—Shervin Nakhjavan
(74) *Attorney, Agent, or Firm*—George A. Leone

(57) ABSTRACT

A parallel-beam optical tomography system for imaging an object of interest includes a parallel ray beam radiation source that illuminates the object of interest with a plurality of parallel radiation beams. After passing through the object of interest the pattern of transmitted or emitted radiation intensities is magnified by a post specimen optical element or elements. An object containing tube is located within an outer tube, wherein the object of interest is held within or flows through the object containing tube. A motor may be coupled to rotate and/or translate the object containing tube to present differing views of the object of interest. One or more detector arrays are located to receive the emerging radiation from the post specimen magnifying optic. Two- or three-dimensional images may be reconstructed from the magnified parallel projection data.

56 Claims, 12 Drawing Sheets

U.S. PATENT DOCUMENTS

| | | | | |
|---|---|---|---|---|
| 4,209,827 A | 6/1980 | Duinker | | 378/21 |
| 4,293,221 A | 10/1981 | Kay | | 356/318 |
| 4,360,885 A | 11/1982 | Edgar | | 382/131 |
| 4,422,146 A | 12/1983 | Yamaguchi | | 378/22 |
| 4,873,653 A | 10/1989 | Grosskopf | | 359/371 |
| 4,891,829 A | * 1/1990 | Deckman et al. | | 378/4 |
| 5,141,609 A | 8/1992 | Sweedler et al. | | 204/452 |
| 5,148,502 A | 9/1992 | Tsujiuchi et al. | | 382/255 |
| 5,281,517 A | 1/1994 | Bacus et al. | | 435/6 |
| 5,308,990 A | 5/1994 | Takahashi et al. | | 250/459.1 |
| 5,312,535 A | 5/1994 | Waska et al. | | 204/603 |
| 5,321,501 A | 6/1994 | Swanson et al. | | 356/479 |
| 5,402,460 A | 3/1995 | Johnson | | 378/10 |
| 5,421,330 A | 6/1995 | Thirion | | 600/425 |
| 5,668,887 A | 9/1997 | Parker et al. | | 204/603 |
| 5,680,484 A | 10/1997 | Ohyama et al. | | 382/255 |
| 5,710,429 A | 1/1998 | Alfano et al. | | 382/108 |
| 5,739,540 A | 4/1998 | Motomura | | 250/363.04 |
| 5,741,411 A | 4/1998 | Yeung et al. | | 250/358.1 |
| 5,760,901 A | 6/1998 | Hill | | 356/450 |
| 5,760,951 A | 6/1998 | Dixon et al. | | 359/385 |
| 5,828,408 A | 10/1998 | Mottin et al. | | 348/295 |
| 5,848,123 A | 12/1998 | Strommer | | 378/98.8 |
| 5,878,103 A | 3/1999 | Sauer et al. | | 378/115 |
| 5,880,838 A | 3/1999 | Marx et al. | | 204/452 |
| 5,909,476 A | 6/1999 | Cheng et al. | | 378/4 |
| 5,915,048 A | 6/1999 | Hill et al. | | 382/255 |
| 5,987,158 A | 11/1999 | Meyer | | 382/133 |
| 6,005,617 A | 12/1999 | Shimamoto et al. | | 348/295 |
| 6,026,174 A | 2/2000 | Palcic | | 382/133 |
| 6,038,067 A | 3/2000 | George | | 359/368 |
| 6,047,080 A | 4/2000 | Chen et al. | | 382/128 |
| 6,072,624 A | 6/2000 | Dixon et al. | | 359/385 |
| 6,091,983 A | 7/2000 | Alfano et al. | | 600/431 |
| 6,130,958 A | 10/2000 | Rohler et al. | | 382/131 |
| 6,165,734 A | 12/2000 | Garini | | 435/7.21 |
| 6,201,628 B1 | 3/2001 | Basiji | | 359/212 |
| 6,211,955 B1 | 4/2001 | Basiji | | 356/326 |
| 6,215,587 B1 | 4/2001 | Alfano et al. | | 359/368 |
| 6,248,988 B1 | 6/2001 | Krantz | | 250/201.3 |
| 6,249,341 B1 | 6/2001 | Basiji | | 356/73 |
| 6,251,586 B1 | 6/2001 | Mulshine | | 435/6 |
| 6,251,615 B1 | 6/2001 | Oberhardt | | 435/7.21 |
| 6,252,979 B1 | 6/2001 | Lee | | 382/133 |
| 6,312,914 B1 | * 11/2001 | Kardos et al. | | 435/6 |
| 6,388,809 B1 | 5/2002 | MacAulay | | 359/383 |
| 6,452,179 B1 | 9/2002 | Coates et al. | | 250/339.09 |
| 6,529,614 B1 | 3/2003 | Chao et al. | | 382/103 |
| 6,741,730 B2 | 5/2004 | Rahn | | 382/131 |
| 2001/0012069 A1 | 8/2001 | Derndinger et al. | | 348/295 |
| 2002/0141625 A1 | 10/2002 | Nelson | | 382/131 |
| 2002/0161534 A1 | 10/2002 | Adler et al. | | 702/35 |
| 2003/0199758 A1 | 10/2003 | Nelson | | 600/425 |

OTHER PUBLICATIONS

RH Anderson, "Close–up imaging of documents and displays with lens arrays," *Applied Optics* 18, 477 (1979).

Kak, A.C. and Slaney, M.,*Principles of Computerized Tomographic Imaging*, IEEE Press, New York, 1988.

E.G. Steward, *Fourier Optics: An Introduction*, 2nd ed. (Halsted Press, New York, 1987).

A. Klug and J.L. Finch, "Structure of viruses of the papilloma–polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three–dimensional diffuse optical tomography of bones and joints," J. Biomed. Optics, vol. 7, p. 88 (2002).

H. Banda–Gamboa et al., "Spectral–Analysis of Cervical Cells Using the Discrete Fourier–Transform," Anal. Cell. Path., vol. 5(2), pp. 85–102 (1993).

D.E. Burger, et al., "Extraction of Morphilogical Features from Biological Models and Cells by Fourier Analysis of Static Light Scatter Measurements," Cytometry, vol. 2, No. 5, pp. 327–336 (1982).

M. Rozycka, et al., "Optical Diffraction as a Tool for Semiautomatic, Quantitative Analysis of Tissue Specimens," Cytometry, vol. 2, No. 4, pp. 244–248 (1982).

Almeida and Fuji, Fourier transform differences and averaged simularities in diatoms, Applied Optics, vol. 18, No. 10, pp. 1663–1667, (1979).

Smolinska and Dawidowicz, "Extraction of common or different part from optical images," Institute of Physics, Warsaw Technical University, 222–223.

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149–156, 1981.

Dziedzic–Goclawska, et al., "Application of the Optical Fourier Transform for Analysis of the Spatial Distribution of Collagen Fibers in Normal and Osteopetrotic Bone Tissue," Histochemistry (1982) 74:123–137.

Ostrowski, et al., "Application of Optical Diffractometry in Studies of Cell Fine Structure," Histochemistry (1983) 78:435–449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18–24 (1986).

Bem, W, et al., "Modification of Chromatin Pattern in the Course of Terminal Differentiation During Human Granulocytopiesis: Optical Diffractometry Study," Cellular and Molecular Biology 33(5), 563–571 (1987).

Rozycka, M, et al., "Analysis of chromatin pattern in blood lymphocytes of healthy donors and in lymphoid cells of patients with chronic lymphocytic leukaemia," J. Clin. Pathol. 1988:41:504–509.

George, JS et al., "Virtual Pinhole Confocal Microscope," Physics Division Progress Report, www.lanl.gov/p/pdfs.papp_pinhole.pdf, (1999–2000).

Pawley, JB, *Handbook of Biological Confocal Microscopy*, Plenum Press, NY, 479–490 (1995).

Kikuchi, S. et al., "Three–dimensional computed tomography for optical microscopes," Optics Communications 107 (1994) 432–444.

Kikuchi, S. et al., "Three–dimensional microscopic computed tomography based on general Radon transform for optical imaging systems," Optics Communications 123 (1996).

Matula, P. et al. " Precise 3D image alignment in micro–axial tomography," Journal of Microscopy, vol. 209, Pt. 2 (Feb. 2003) pp. 126–142.

Ong, SH, Development of an imaging flow cytometer. Anal Quant Cytol Histol 9(5)pp. 375–382, 1987.

Gilbert, P, "Iterative Methods for the Three dimensional Reconstruction of an Object from Projections," Journal of Theoretical Biology 36pp. 105–117, 1972.

Oppenheim, BE, More Accurate Algorithms for Iterative 3 dimensional Reconstruction, IEEE Transactions on Nuclear Science NS–21pp. 72–77, 1974.

Singer, Jr, Grunbaum, FA, Kohn, P, and Zubelli, JP, "Image Reconstruction of the Interior of Bodies that Diffuse Radiation," Science 248(4958)pp. 990–993, 1990.

Mueller, K and Yage, R, "Rapid 3–D Cone–beam Reconstruction with the Simultaneous Algebraic Reconstruction Technique (SART) Using 2–D Texture Mapping Hardware", IEEE Transactions on Medical imaging 19(12)pp. 1227–1237, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32pp. 205–216, 1971.

Manglos, SH, Jaszcak, RJ, and Floyd, CE, "Maximum Likelihood Reconstruction for Cone Beam SPECT: Development and Initial Tests," Physics in Medicine and Biology 34(12)pp. 1947–1957,1989, #1382.

Manglos, SH, Gagne, GM, Krol A, Thomas, FD, and Narayanaswamy, R, "Transmission Maximum–likelihood Reconstruction with Ordered Subsets for Cone Beam CT", Physics in Medicine and Biology 40(7)pp. 1225–1241, 1995, #4389.

Hampel, U and Freyer, R, "Fast Image Reconstruction for Optical Absorption Tomography in Media with Radially Symmetric Boundaries", Medical Physics 25 (1)pp. 92–101, 1998.

Jiang, H, Paulsen, KD, and Osterberg, UL, "Frequency–domain Near–infrared Photo Diffusion Imaging: Initial Evaluation in Multitarget Tissuelike Phantoms", Medical Physics 25(2)pp. 183–193,1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691–701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, $3^{rd}$ ed., Wiley-Liss, 1995.

Bayat, S, Le Duc, G, Porra, L, Berrruyer, G, Nemoz, C, Monfraix, S, Fiedler, S, Thomlinson, W, Suortti, P, Standertskjold–Nordenstam, CG, and Sovijarvi, ARA, "Quantitative Functional Lung Imaging with Synchrotron Radiation Using Inhaled Xenon as Contrast Agent", Physics in Medicine and Biology 46(3287–99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267–R1279) 2002.

Cheng, PC, Lin, TH, Wang, G, Shinozaki, DM, Kim, HG, and Newberry, SP, "Review on the Development of Cone–beam X–ray Microtomography", Proceedings of the X–ray Optics and Microanalysis 1992, Institute of Physics Ser. No. 130, Kenway, PB, et al. (eds.), Manchester, UK, Aug. 31–Sep. 4, 1992, pp. 559–566.

Defrise, M, Clack, R, and Townsend, DW, "Image Reconstruction from Truncated, Two–dimensional, Parallel Projections", Inverse Problems 11(287–313) 1995.

Defrise, M, Noo, F, and Kudo, H, "A Solution to the Long–object Problem in Helical Cone–beam Tomography", Physics in Medicine and Biology 45(623–43) 2000.

Endo, M, Tsunoo, T, Nakamori, N, and Yoshida, K, "Effect of Scattered Radiation on Image Noise in Cone Beam CT", Medical Physics 28(4) (469–74) 2001.

Jorgensen, SM, Demirkaya, O, and Ritman, EL, "Three Dimensional Imaging of Vasculature and Parenchyma in Intact Rodent Organs with X–ray Micro–CT", Am. J. Physiology 275(Heart Circ. Physiol. 44) pp. H1103–H1114, 1998.

Kinney, JH, Johnson, QC, Saroyan, RA, Nichols, MC, Bonse, U, Nusshardt, R, and Pahl, R, "Energy–modulated X–ray Microtomography", Rev. Sci. Instrum. 59(1)pp. 196–197, 1988.

Kinney, JH and Nichols, MC, "X–ray Tomographic Microscopy (XTM) Using Synchrotron Ratiation", Annu. Rev. Mater. Sci. 22pp. 121–152, 1992.

Taguchi, K and Aradate, H, "Algorithm for Image Reconstruction in Multi–slice Helical CT", Medical Physics 25(4) pp. 550–561, 1998.

Yu, DF, Fessler, JA, and Ficaro, EP, "Maximum–Likelihood Transmission Image Reconstruction for Overlapping Transmission Beams", IEEE Transactions on Medical Imaging 19(11)pp. 1094–1105, 2000.

* cited by examiner

OPTICAL TOMOGRAPHY OF SMALL OBJECTS USING PARALLEL RAY ILLUMINATION AND POST-SPECIMEN OPTICAL MAGNIFICATION

RELATED APPLICATION

This application is a continuation-in-part of co-pending U.S. application Ser. No. 09/927,151 of Alan C. Nelson, filed Aug. 10, 2001, issued on Feb. 18, 2003 as U.S. Pat. No. 6,522,775, that is in turn related to the provisional application of Alan C. Nelson, Ser. No. 60/279,244, filed Mar. 28, 2001, both entitled "APPARATUS AND METHOD FOR IMAGING SMALL OBJECTS IN A FLOW STREAM USING OPTICAL TOMOGRAPHY."

This application is also related to U.S. Pat. No. 6,591,003, issued Jul. 8, 2003 to Chu, entitled "OPTICAL TOMOGRAPHY OF SMALL MOVING OBJECTS USING TIME DELAY AND INTEGRATION IMAGING."

FIELD OF THE INVENTION

The present invention relates to optical tomographic (OT) imaging systems in general, and, more particularly, to parallel-beam optical tomography (PBOT) where a small object, such as a biological cell, for example, is illuminated by an intense, parallel beam in the visible or ultraviolet portion of the electromagnetic spectrum and magnified transmitted or emission projected images are produced by means of post-specimen magnification optics.

BACKGROUND OF THE INVENTION

U.S. application Ser. No. 10/126,026 of Alan C. Nelson, filed Apr. 19, 2002, entitled "VARIABLE-MOTION OPTICAL TOMOGRAPHY OF SMALL OBJECTS" is incorporated herein by this reference. In Nelson, projection images of shadowgrams are digitally captured by means of conventional image detectors such as CMOS or CCD detectors. In imaging moving objects, such image sensors require short exposures to "stop motion" in order to reduce motion blur. Short exposures limit the signal to noise ratio that can be attained when imaging moving objects.

Nelson's patent applications teach cone beam projection images or shadowgrams generated using sub-micron point sources of illumination and captured using CCD or CMOS image detectors. Cone beam illumination and projection geometry possesses the desirable characteristic that the transmitted projection image is magnified by virtue of the divergence, in two dimensions, or one dimension in the case of fan beam geometry, of the light ray paths in the beam. The aforesaid arrangement allows improvement of the resolution limitation that might otherwise be imposed by a detector pixel size, and the spatial resolution in the projections is ultimately limited by either the source aperture diameter or the wavelength of the illumination, whichever is greater. Cone beam geometry for projection and tomographic imaging has been utilized in diagnostic and other x-ray imaging applications (Cheng, P C, Lin, T H, Wang, G, Shinozaki, D M, Kim, H G, and Newberry, S P, "Review on the Development of Cone-beam X-ray Microtomography", Proceedings of the X-ray Optics and Microanalysis 1992, Institute of Physics Conference Series Volume 130, Kenway, P B, et al. (eds.), Manchester, UK, Aug. 31–Sep. 4, 1992, pp.559–66; Defrise, M, Clack, R, and Townsend, D W, "Image Reconstruction from Truncated, Two-dimensional, Parallel Projections", Inverse Problems 11:287–313, 1995; Defrise, M, Noo, F, and Kudo, H, "A Solution to the Long-object Problem in Helical Cone-beam Tomography", Physics in Medicine and Biology 45:623–43, 2000; Endo, M, Tsunoo, T, Nakamori, N, and Yoshida, K, "Effect of Scattered Radiation on Image Noise in Cone Beam CT", Medical Physics 28(4):469–74, 2001; Taguchi, K and Aradate, H, "Algorithm for Image Reconstruction in Multi-slice Helical CT", Medical Physics 25(4):550–61, 1998). There it arises naturally, since x-rays from thermally-assisted tungsten filament, electron-impact, laboratory or clinical diagnostic radiology sources invariably diverge from the point on the target anode that is bombarded by the accelerated electrons. Since the discovery of x-rays in 1895, the vast majority of x-ray sources have operated on the mechanisms of Bremsstrahlung and characteristic x-ray production. Except for synchrotrons, which are elaborate and expensive devices inaccessible to most research and healthcare professionals, parallel-beam x-ray sources are not available in the portions of the x-ray spectrum usually employed in clinical and scientific imaging applications. There are, however, lasers and other relatively inexpensive sources capable of producing intense, parallel-ray illumination in the visible and ultraviolet portions of the spectrum.

A number of researchers have employed parallel-beam geometry to perform synchrotron and laboratory x-ray microtomography (micro-CT). (See, for example, Bayat, S, Le Duc, G, Porra, L, Berruyer, G, Nemoz, C, Monfraix, S, Fiedler, S, Thomlinson, W, Suortti, P, Standertskjold-Nordenstam, C G, and Sovijarvi, A R A, "Quantitative Functional Lung Imaging with Synchrotron Radiation Using Inhaled Xenon as Contrast Agent", Physics in Medicine and Biology 46:3287–99, 2001; Kinney, J H, Johnson, Q C, Saroyan, R A, Nichols, M C, Bonse, U, Nusshardt, R, and Pahl, R, "Energy-modulated X-ray Microtomography", Review of Scientific Instruments 59(1):196–7, 1988. Kinney, J H and Nichols, M C, "X-ray Tomographic Microscopy (XTM) Using Synchrotron Radiation", Annual Review of Material Science 22:121–52, 1992; Jorgensen, S M, Demirkaya, O, and Ritman, E L, "Three Dimensional Imaging of Vasculature and Parenchyma in Intact Rodent Organs with X-ray Micro-CT", American Journal of Physiology 275(Heart Circ. Physiol. 44):H1103–14, 1998; Bentley, M D, Ortiz, M C, Ritman, E L, and Romero, J C, "The Use of Microcomputed Tomography to Study Microvasculature in Small Rodents", American Journal of Physiology (Regulatory Integrative Comp Physiol) 282:R1267–R1279, 2002).

A syncrotron beam may be monochromatized using crystals or other optical elements from which it emerges with extremely low divergence. In the laboratory setting, with conventional microfocal x-ray sources, if the specimen or object is placed far from an intense x-ray source, it intercepts a relatively small cone of x-rays and the projection geometry may be approximated as parallel with only minimal detriment to the resulting image quality, though flux at the specimen is very low. Synchrotrons produce enormously intense radiation that facilitates relatively rapid scan times (e.g. scan times of seconds or minutes) for 3D microtomography. Unfortunately, synchrotron-based microtomography devices are very expensive. Electron-impact laboratory or clinical sources of the types described above are of much lower intensity relative to synchrotrons. In such systems, divergence of the beam and small cone angle subtended by a specimen placed remotely from the source in order to approximate the parallel geometry result in very low fluence at the specimen and commensurately long scan times of, for example, hours to days.

Although useful for various applications, cone beam projection geometry has some drawbacks. For example, the achievable spatial resolution is limited by the source size, thus mandating a sub-micron source for microscopic and cellular imaging. Further, the fluence or number of photons per unit area in the beam available from a sub-micron point source is very low, thereby placing stringent demands on the sensitivity and noise characteristics of the detector if adequate image quality and signal-to-noise ratio are to be obtained in the projection images. It is challenging to produce the sub-micron source size necessary to provide sub-micron resolution for cone beam imaging. Reproducibly fabricating such sub-micron light sources that produce relatively uniform or gaussian beam intensity profiles presents a significant challenge. For example, in some cases it is necessary to draw laser diode-pigtailed, single-mode optical fibers to a tapered tip. In other cases small apertures or microlenses must be placed between lasers or laser diodes or alternative light sources and the specimen. For optimal imaging and accurate image reconstruction, it is advantageous that the imaged object be positioned centrally in the cone beam, precisely aligned with the source position.

In the cone beam imaging geometry, projection magnification is strongly dependent upon the source-to-specimen distance, which is not the case in a parallel imaging geometry. In a dynamic flow tomographic imaging system, as described in the referenced Nelson patents, where the source-detector pairs may be disposed about a reconstruction cylinder in a variety of geometric arrangements, source-to-specimen distances must be precisely controlled and known to a high degree of accuracy for all source-detector pairs. Differing source-to-specimen distances between the source-detector pairs may result in degradation of the reconstructed image quality. Because projection magnification varies through the object space in cone beam imaging, the two-dimensional projection images or shadowgrams may be difficult to interpret. For example, it may be difficult to extract diagnostically-relevant features from the projection images directly. Cone beam projection geometry also requires 3D image reconstruction algorithms and computer programs that are complex and computationally intensive.

SUMMARY OF THE INVENTION

The present invention provides a parallel-beam optical tomography system for imaging an object of interest including a parallel ray beam radiation source for illuminating the object of interest with a plurality of parallel radiation beams. An object containing tube is located to be illuminated by the parallel ray beam radiation source, wherein the object of interest is held within the object containing tube such that when it is illuminated by the plurality of parallel radiation beams, radiation emerges from the object containing tube. A detector array is located to receive the emerging radiation pattern that may be magnified prior to imaging upon the detector.

In one contemplated embodiment, a parallel ray beam radiation source illuminates the object of interest with a plurality of parallel radiation beams. An outer tube has an optically flat input surface for receiving the illumination and a concave output surface, where the concave outer surface acts as a magnifying optic to diverge the radiation emerging from the outer tube after passing through the object of interest. An object containing tube is located within the outer tube, wherein the object of interest is held within the object containing tube. A motor is coupled to rotate and otherwise manipulate the object containing tube to present differing views of the object of interest. A detector array is located to receive the emerging radiation from the concave output surface.

The present invention relates generally to three-dimensional optical tomography using parallel beam projections produced by a laser or other illumination system in conjunction with CCD or CMOS detectors and, more particularly, to three dimensional tomographic imaging of microscopic objects, including biological cells, in a flow stream or entrained in a rigid medium.

One motivation of this invention is to improve the signal-to-noise ratio in the projections and two-dimensional or three-dimensional reconstructed images in dynamic optical tomography systems by using available intense parallel-beam illumination sources in the visible and ultraviolet portions of the electromagnetic spectrum.

One advantage of the method and system described herein, relative to a similar system employing divergent cone beam illumination geometry, is that it provides a PBOT system where achievable image resolution is substantially independent of source aperture size.

Another advantage of the present invention, relative to a similar system employing divergent cone beam illumination geometry, is that it provides a PBOT system wherein a submicron source diameter is not required.

Another advantage of the present invention, relative to a similar system employing divergent cone beam illumination geometry, is that it provides a PBOT system wherein intensity distribution through a beam cross section can be more easily controlled and made more uniform or more nearly gaussian.

Another advantage of the present invention, relative to a similar system employing divergent cone beam illumination geometry, is that it provides a PBOT system wherein illumination intensity, herein also called fluence, at the specimen is increased by orders of magnitude.

Another advantage of the present invention, relative to a similar system employing divergent cone beam illumination geometry, is that it provides a PBOT system wherein signal-to-noise ratios achievable in the projection and reconstructed images is significantly higher.

Another advantage of the present invention, relative to a similar system employing divergent cone beam illumination geometry, is that it provides a PBOT system wherein required illumination sources can be more easily and reproducibly fabricated.

Another advantage of the present invention, relative to a similar system employing divergent cone beam illumination geometry, is that it provides a PBOT system wherein geometrical constraints and spatial tolerances required in terms of the location of system components relative to the imaged sample, most importantly the source-to-specimen distance, are considerably relaxed.

Another advantage of the present invention, relative to a similar system employing divergent cone beam illumination geometry, is that it provides a PBOT system wherein the precision of the temporal synchronization required for the strobing or pulsing of the source, the projection image acquisition by the sensor, and the passage of the specimen through the imaged volume between the sources and detectors is considerably lowered.

Another advantage of the present invention, relative to a similar system employing divergent cone beam illumination geometry, is that it provides a PBOT system requiring lower precision for source location.

Yet another advantage of the present invention, relative to a similar system employing divergent cone beam illumination geometry, is that it provides a PBOT system wherein projection image magnification is substantially constant through an object space, so as to make potentially diagnostic image features such as densities, areas and volumes in the projection images easier to interpret and accurately quantify.

Another advantage of the present invention, relative to a similar system employing divergent cone beam illumination geometry, is that it provides a PBOT system wherein selected individual transaxial images, or slices through the imaged object may be reconstructed from a subset of the data acquired by the two-dimensional sensor arrays.

Still another advantage of the present invention, relative to a similar system employing divergent illumination geometry and a cone beam reconstruction algorithm, is that it provides a PBOT system wherein the complexity and computational intensity of the reconstruction algorithm, whether of the analytical convolution backprojection, iterative, statistical or other type, are substantially reduced, and degradations in the images caused by the reconstruction process itself are ameliorated.

DETAILED DESCRIPTION OF THE PREFERRED EMBODIMENTS

The invention is described herein with respect to specific examples relating to biological cells. It will be understood, however, that these examples are for the purpose of illustrating the principals of the invention, and that the invention is not so limited. In one example, constructing a three dimensional distribution of optical densities within a microscopic volume enables the quantification and the determination of the location of structures, molecules or molecular probes of interest. By using tagged molecular probes, the quantity of probes that attach to specific structures in the microscopic object may be measured. For illustrative purposes, an object such as a biological cell may be labeled with at least one stain or tagged molecular probe, and the measured amount and location of this probe may yield important information about the disease state of the cell, including, but not limited to, various cancers such as lung, breast, prostate, cervical and ovarian cancers.

One feature of the present invention is that the chosen illumination is parallel, or nearly parallel, until after passage through the object volume that may contain the cell or other specimen or object to be imaged. After passage through the object, a post-specimen optic diverges the emergent pattern of light intensities in order to produce a magnified pattern of light intensities in any plane perpendicular to the system's optical axis and situated downstream from the post-specimen optic.

Figure 1:
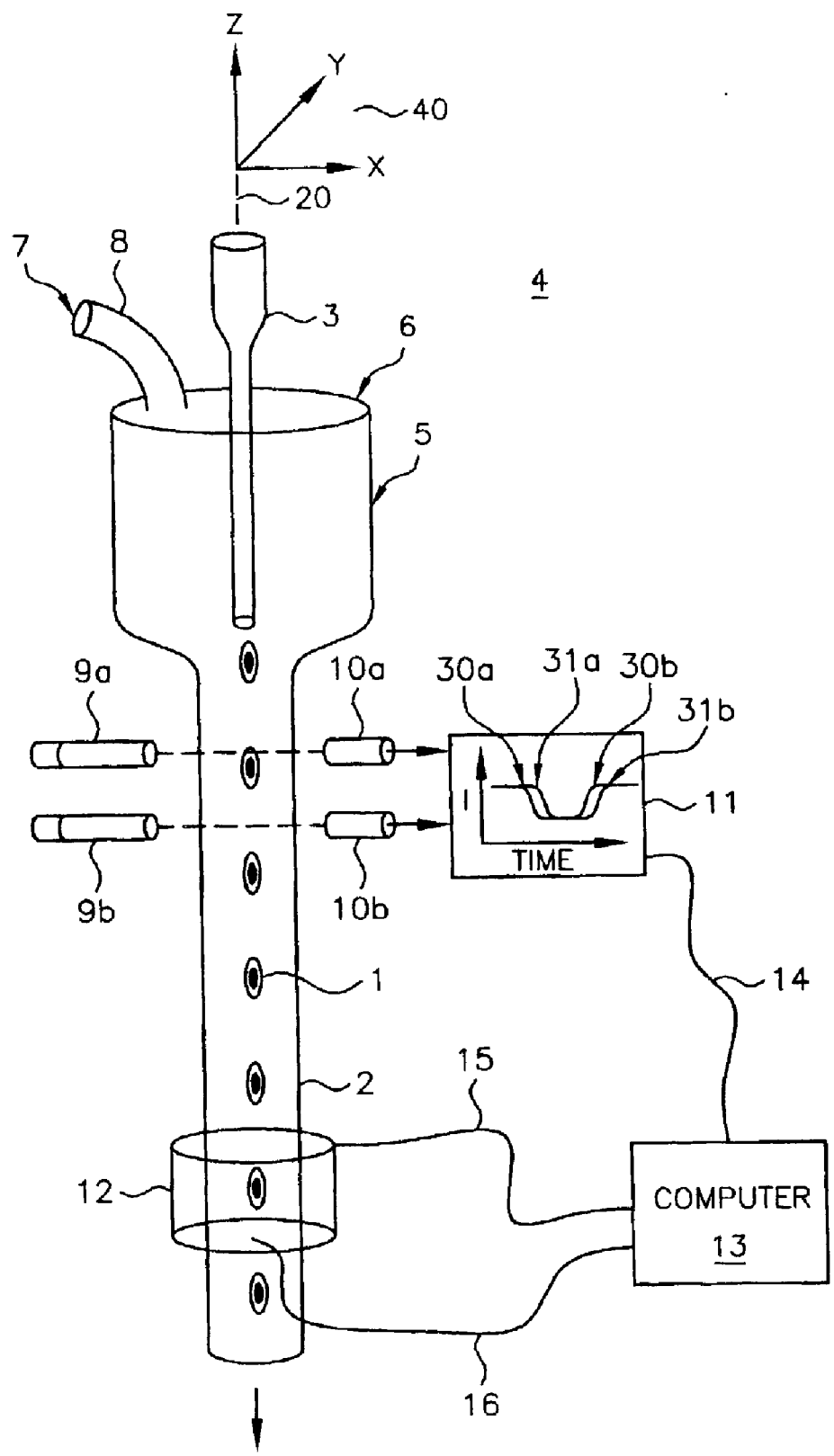
FIG. 1 schematically shows an example illustration of a Parallel Beam Flow Optical Tomography system as contemplated by an embodiment of the present invention.

Referring to FIG. 1, there schematically shown is an example illustration of a Parallel Beam Flow Optical Tomography (PBOT) system as contemplated by an embodiment of the present invention. The invention provides an apparatus and method for imaging small objects in a flow stream or entrained in a rigid medium using optical point source or parallel beam projections, image sensors, such as, for example, time delay and integration (TDI) image sensors or CCD or CMOS solid state image sensors and the like, and tomographic image reconstruction. The optical tomography (OT) system includes in one example embodiment, a flow cytometer, including a reconstruction cylinder 12, positioned around object containing tube 2. The object containing tube 2 may, for example, comprise a cell entrainment tube wherein the cell is held in a gel, or a capillary tube for cell flow, depending on the type of optical tomography system.

The PBOT system 4 is oriented with reference to a coordinate system 40 having coordinates in the X, Y and Z-directions. In operation, an object of interest 1, such as, for example a cell, including a human cell, is injected into an injection tube 3. The object containing tube 2 may be wider at an injection end 5 and includes a pressure cap 6. A sheath fluid 7 is introduced at tube 8 to create laminar flow within the object containing tube 2. A first source of photons 9a and a first photo detector 10a work together with a pulse height analyzer 11 to operate as a triggering device. Pulse height analyzer 11 operates to provide a first signal 30a for the beginning or leading edge of an object, such as a cell, and a second signal 30b for the end or trailing edge of the object as it moves through the tube. The signals 30a, 30b, 31a and 31b are represented as a light intensity, "I" versus "TIME" function within pulse height analyzer 11. The pulse height analyzer 11 may be a conventionally designed electronic circuit or the like. The pulse height analyzer 11 generates a plurality of signals 14 that are sent to a computer 13 which, after a delay related to the velocity of the moving object and distance between the photo detector and the reconstruction cylinder 12, sends a trigger signal on line 15 to a reconstruction cylinder 12 to initiate and terminate data collection for that particular object of interest. Additionally, a second photon source 9b and a second photo detector 10b may advantageously be positioned at a known distance downstream from the first set such that an interval between the object triggering a third signal 31a and triggering a fourth signal 31b may advantageously be used to calculate the velocity of the object and also as a timing signal to synchronize the line transfer rate of a TDI image sensor. The timing signal is transmitted to computer 13 in the plurality of signals 14. The computer 13, which may be any useful personal computer or equivalent, in turn sends synchronization signals on line 16 to the reconstruction cylinder 12. It will be understood that lines 15 and 16 are representative of communication and control lines between the PBOT system and the computer that communicate data, image information, control signals and other signals between the computer and the PBOT system. In this way, for example, the movement of the object along the flow axis 20 may be matched by a rate of transfer of charge from one stage of a TDI sensor to the next, as described and shown in more detail below with reference to FIG. 7.

Figure 2:
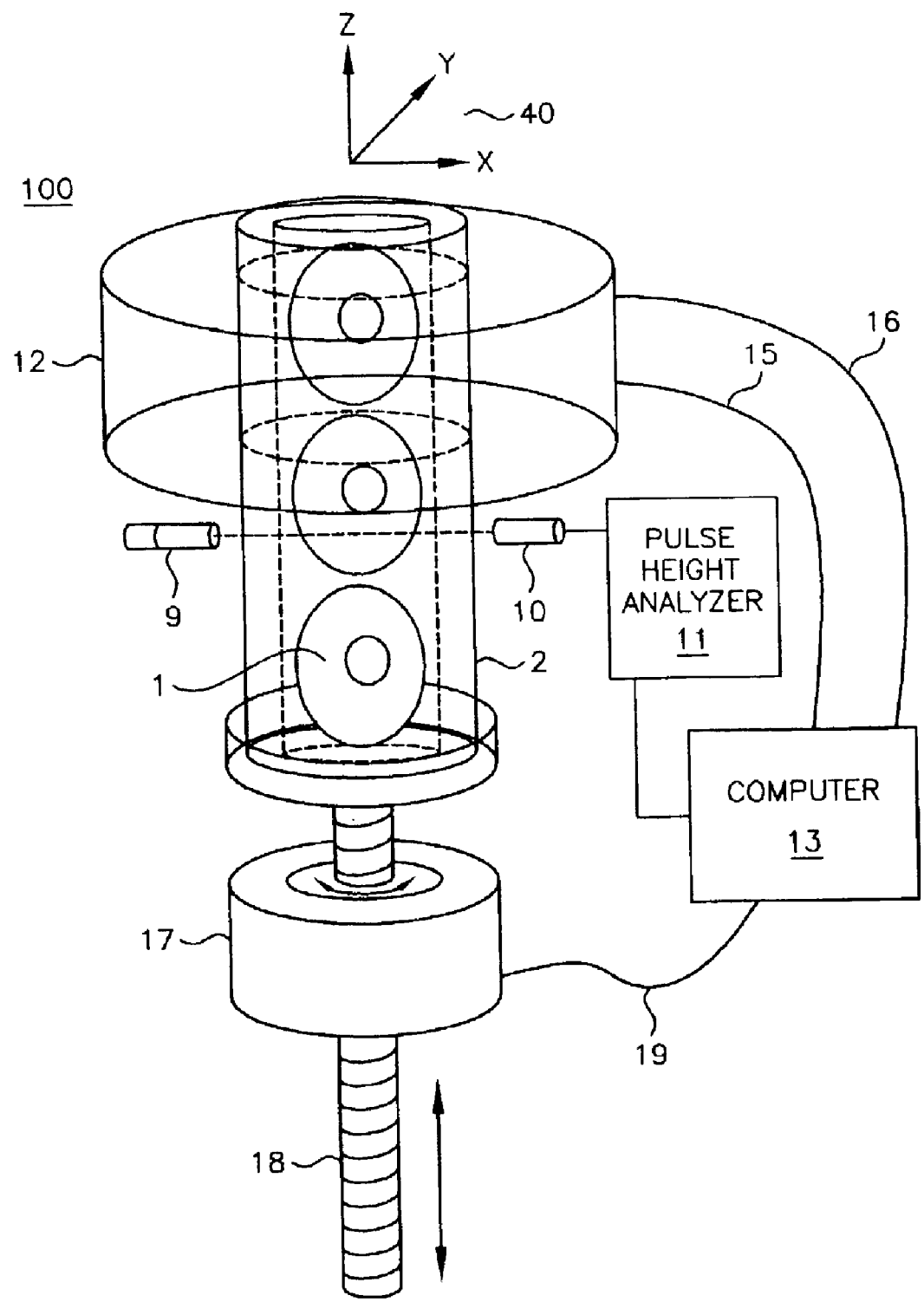
FIG. 2 schematically shows an example illustration of a Variable Motion Parallel Beam Optical Tomography system as contemplated by an embodiment of the present invention.

Now referring to FIG. 2, there schematically shown is an example illustration of a Variable Motion Parallel Beam Optical Tomography system as contemplated by one example embodiment of the present invention. A variable motion PBOT system 100 takes advantage of a mechanical positioner to present cells, which are entrained in a rigid medium in a tube, to the imaging system one at a time. As compared to the flow system described with reference to FIG. 1, in the variable motion PBOT system 100 only one trigger mechanism including a photon source 9 and a photo detector 10 is required since the velocity of the object, such as a human cell, can be precisely controlled to synchronize with the illumination sources and image sensors in the reconstruction cylinder 12. The trigger here is processed by the pulse height analyzer 11 and the computer 13 and used to start and stop data collection. The pulse height analyzer 11 is an electronic circuit of design similar to pulse height analyzer 11 except that it requires fewer inputs and outputs. As indicated by double arrow line the object containing tube 2 in this embodiment is translated along the z-axis through the reconstruction cylinder 12 by a screw drive 18 driven by a computer controlled motor 17. The object contained in tube 2 may also be rotated about the z-axis by the computer controlled motor 17. The computer controlled motor 17 receives control information 19 from the computer 13. It will be understood by those skilled in the art having the benefit of this disclosure, that any mechanism capable of translating and rotating the object containing tube 2 can be used in place of the screw drive. Signals from the reconstruction cylinder 12 may be analyzed directly or processed using image processing, image analysis and/or computerized tomographic image reconstruction techniques to provide two dimensional or three dimensional information about cells and other objects of interest.

Figure 3:
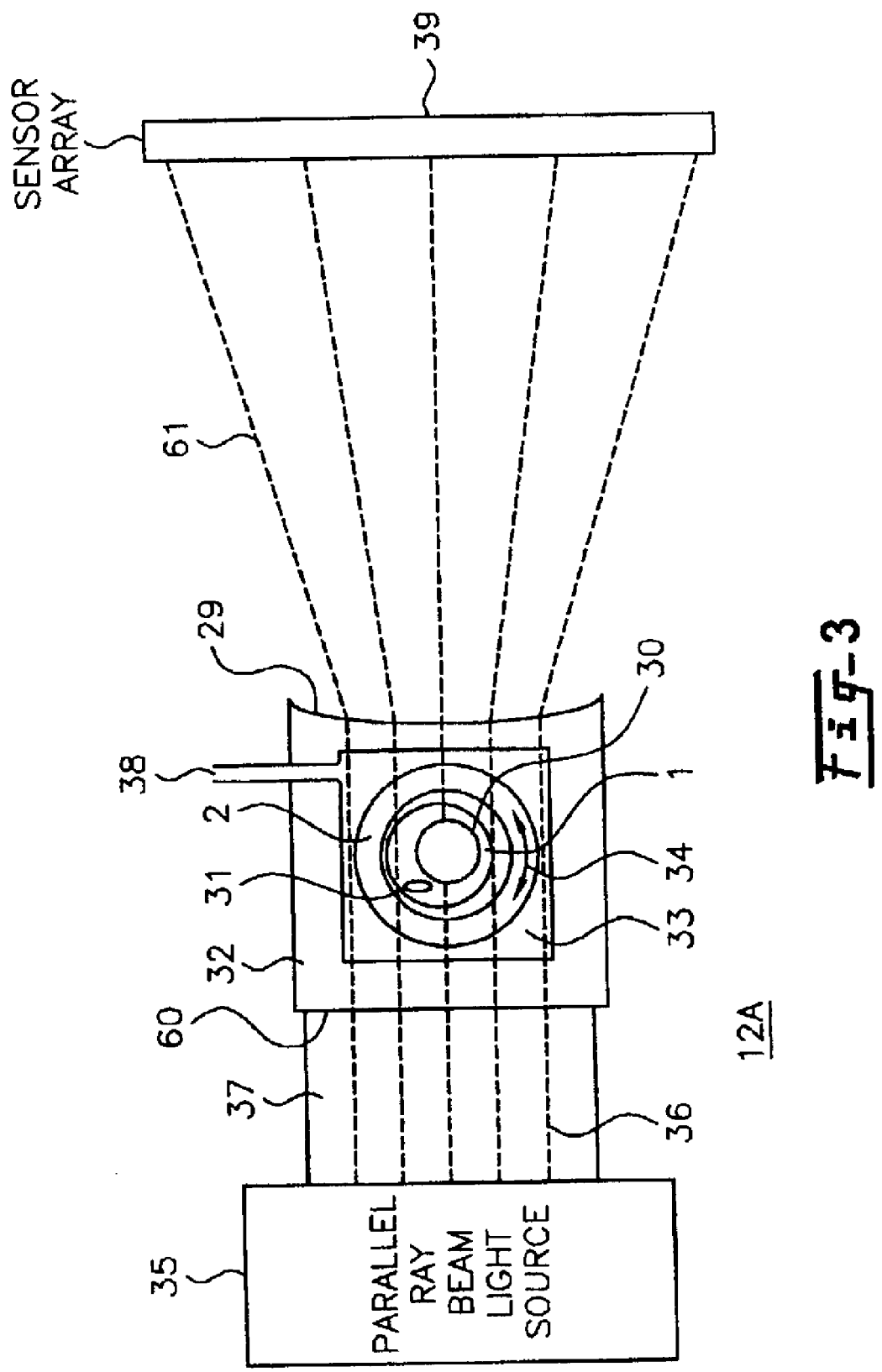
FIG. 3 schematically shows an example illustration of a system illumination geometry, including a single source-magnifying concave optic pair as contemplated by one example embodiment of the present invention.

Referring now to FIG. 3, a system illumination geometry within a reconstruction cylinder 12A for use in a parallel-beam optical tomography system for imaging an object of interest 1 is shown schematically. The reconstruction cylinder 12A includes a parallel ray beam radiation source 35 for illuminating the object of interest 1 with a plurality of parallel radiation beams 36. An outer tube 32 has an optically flat input surface 60 and a concave output surface 29, where the concave outer surface 29 diverges radiation 61 emerging from the outer tube 32 after passing through the object of interest 1. An object containing tube 2 is located within the outer tube 32, wherein the object of interest 1 is held within the object containing tube 2.

A motor, here indicated schematically as double arrow 34, is coupled to rotate the object containing tube 2 to present differing views of the object of interest 1. A detector array 39 is located to receive the emerging radiation 61 from the concave output surface 29. In one embodiment, the parallel ray beam radiation source 35 comprises a laser. In another example embodiment, the laser may be selected to emit radiation in the visible portion of the electromagnetic spectrum. In yet another example embodiment, the laser may be selected to emit radiation in the ultraviolet portion of the electromagnetic spectrum. The detector array 39 may advantageously comprise a sensor selected from the group consisting of solid state sensors, charge coupled device (CCD) sensors, complementary metal oxide semiconductor (CMOS) sensors and time delay and integration sensors.

In another embodiment of the present invention, a cell or other object to be imaged is present either in a flow tube, capillary tube, linear container, or in an entrainment tube. In one embodiment of the parallel-beam optical tomography system the object of interest 1 comprises a human cell having a nucleus 30. The cell may also contain subcellular features or constituents. At least one fluorescing or absorbing molecular probe 31 may be bound to one or more cellular constituents.

The object containing tube 2, for example a flow tube, capillary tube, linear container, or entrainment tube, is located substantially concentrically within the outer tube 32 which has a substantially rectangular outer cross section, and may have either a rectangular or circular inner cross section. Other cross sectional geometries for the outer tube 32 are possible. The curved surface of the object containing tube 2 acts as a cylindrical lens producing a focusing effect that may not be desirable in a projection system. Those skilled in the art having the benefit of this disclosure will appreciate that the bending of photons by the object containing tube 2 can be substantially reduced if the spaces 37 and 33 between the source and the outer tube 32 and between the tube 32 and the detector surfaces 39 are filled with a material having an index of refraction matching that of the object containing tube 2. Further, the tube can be optically coupled to the space filling material. Such optical coupling may be accomplished with oil or a gel, for example. An index of refraction-matching fluid in space 33, such as oil, for example, may advantageously be introduced through port 38 to entirely fill the space between the tube 2 in which the cells or other microscopic objects are contained and the outer tube 32. The index of refraction matching fluid, both tubes 2 and 32, and any gel or flowing liquid medium surrounding the cells to be imaged have identical, or nearly identical indices of refraction. The object contained within tube 2 may be rotated and/or translated within the index of refraction matching fluid and outer tube 32 with both axial and rotational motions under computer control.

In operation, a laser or other light source 35 produces parallel illuminating beams 36, which impinge on the outer tube 32, optionally delivered by an index of refraction-matched coupling element 37. In the absence of scatter, the light traverses parallel ray paths through both tubes 2 and 32. Since the refractive indices of all materials in the light path are matched, the rays traversing the index of refraction matching fluid and the object space within the volume to be imaged are parallel. Both tubes 2 and 32 comprise transparent, or nearly transparent material with respect to the illuminating wavelength. Both tubes 2 and 32 may comprise fused silica, glass or other similar optical material.

The exit face 29 of the outer, rectangular tube 32 may advantageously be provided with a diverging or magnifying optic, which, in one contemplated embodiment, may be a circularly symmetric polished depression, or dimple, in the fused silica or other optical material. The dimple acts as a plano-concave lens, causing the light ray paths 61 to become divergent at its exit surface 29. Such a dimple or any other optical element or combination of optical elements, including multiplets, or other equivalent elements, designed to perform the same function is referred to herein as a post-specimen optic. The post-specimen optic comprises, generally, a magnifying optic.

Using known optical design principles, the radius of curvature of the post-specimen optic may be determined and designed to impart the desired degree of divergence to the exiting light ray paths 61. The degree of divergence, together with the distance between the post-specimen optic and the TDI, CCD, CMOS or other image sensor 39, determines the magnification of the projection images. The magnification required is determined by the relationship between the desired spatial resolution of the projection images and the detector pixel size, and it is advantageous for the magnification to be much larger than twice the quotient of the pixel size and the desired spatial resolution of the projection.

For example, in one contemplated embodiment of the present invention, if the desired spatial resolution in the projections is 0.5 micron and the detector pixel size is 10 microns, it is advantageous for the magnification to be significantly larger than 40 times. In this example, it may be desirable for the magnification to be 80 times, 100 times, or even more.

For a contemplated embodiment of the current invention in which the post-specimen optic is a circularly symmetric polished dimple on the exit face 29 of the outer tube 32, and in which this post-specimen optic functions as a plano-concave diverging lens, the front focal plane of the lens is at infinity. There is no back focal plane. Thus, a magnified projection image or shadowgram containing information about the absorption of the illumination as it passed through the cell or other object to be imaged 1, can be produced by capturing this emergent pattern of transmitted light intensities on a TDI, CCD or CMOS detector or other digital imaging detector 39. The photo-conversion surface of the detector can be situated in any plane perpendicular to the system's optical axis and downstream from the post-specimen optic. Furthermore, the magnification can be chosen by the placement of the detector plane: the further the detector plane is downstream from the object, the greater the magnification.

Figure 4:
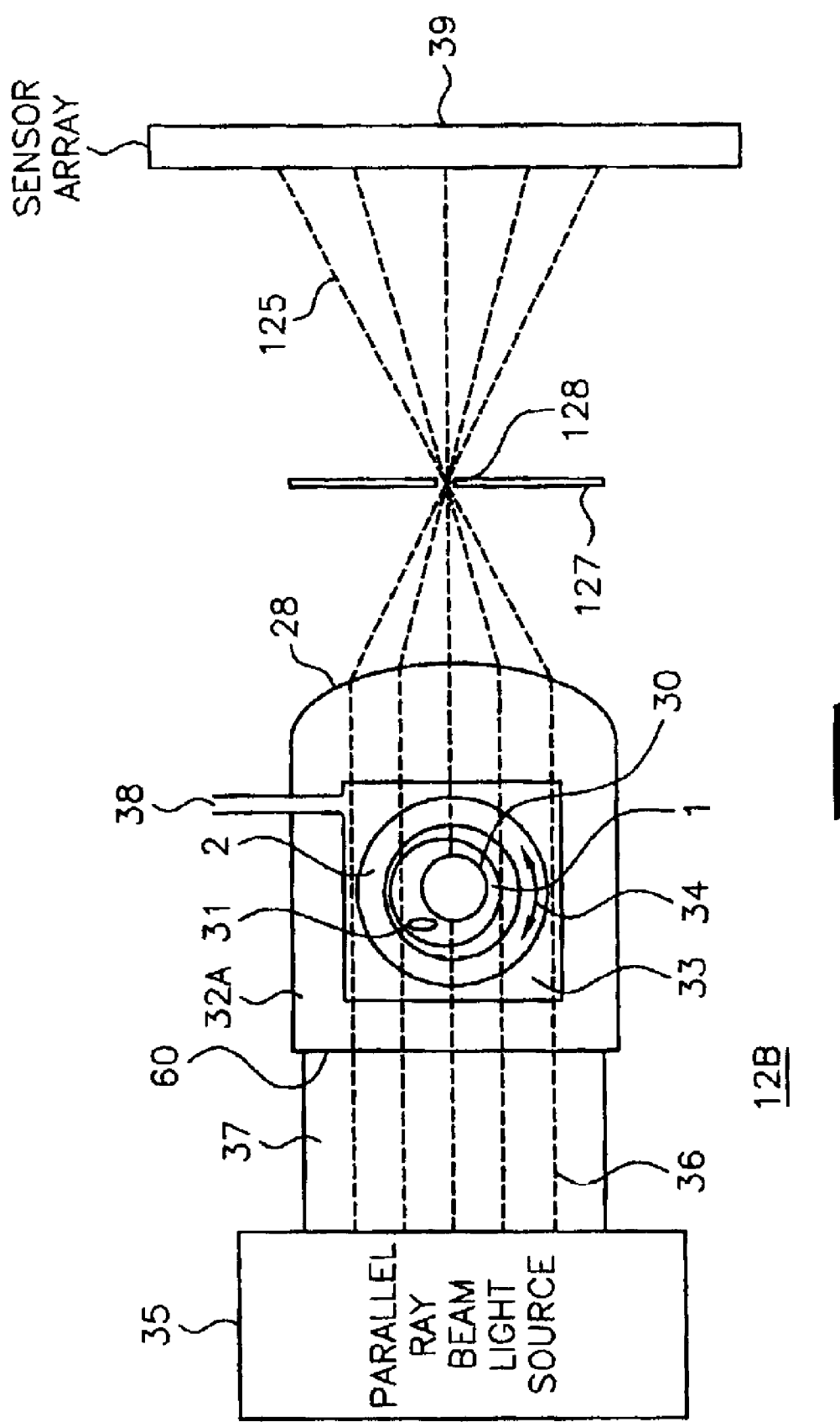
FIG. 4 schematically shows an example illustration of a system illumination geometry, including a single source-magnifying convex optic pair as contemplated by an alternate embodiment of the present invention.

In embodiments of the present invention such as those depicted schematically in FIG. 3 and FIG. 4, having a single source-detector pair, two-dimensional or three-dimensional tomographic imaging of the cell or other microscopic object is performed by obtaining images from varying angles of view. After obtaining a first projection with the object containing tube 2 held stationary at a first rotational angle with respect to the optical axis, the object containing tube 2 may be rotated by a discrete angle about an axis as indicated by the double arrow 34. A useful axis is identified as the Z axis in FIG. 2, and/or pointing out of the page in FIG. 3 and FIG. 4, that is perpendicular to the system's optical axis in order to orient the cell or other object 1 at a second rotational angle with respect to the optical axis. A subsequent transmitted projection image may be obtained after rotation of the object containing tube 2. The process of rotating and imaging may be repeated with the object containing tube 2 repeatedly rotated in discrete increments. A two-dimensional projection image is recorded at each angle until a sufficient number of projections are obtained to produce a three-dimensional image of the cell or other object 1, or portion thereof, or to produce two-dimensional images depicting slices of the absorption pattern in the imaged object's interior.

Three-dimensional reconstructions are produced by image processing of the plurality of two-dimensional projection images with known three-dimensional image reconstruction algorithms. Two-dimensional images of transverse slices through the imaged object are produced by processing lines of data extracted from the plurality of projections, where these lines of data are oriented parallel to rotated versions of the X and Y axes as depicted in FIG. 1 and FIG. 2. The lines of data are generally referred to as rows of detector data. The ability to reconstruct transaxial slices through the cell or other object from rows of detected projection data is an advantage of the method described in the present invention relative to cone beam geometry, in which many lines of detector data would contribute to each transverse image plane through object space.

Referring now to FIG. 4, there shown schematically is an alternate embodiment of a system illumination geometry within a reconstruction cylinder 12B as contemplated by the present invention, where a cell or other object to be imaged 1 may be present in a flow tube or entrainment tube 2. The reconstruction cylinder 12B includes a parallel ray beam radiation source 35 for illuminating the object of interest 1 with a plurality of parallel radiation beams 36. An outer tube 32A has an optically flat input surface 60 and a convex output surface 28, where the convex outer surface 28 focuses radiation emerging from the outer tube 32A after passing through the object of interest 1. As in the above embodiment described with respect to FIG. 3, an object containing tube 2 is located within the outer tube 32A, wherein the object of interest 1 is held within or flows through the object containing tube 2. A motor, indicated schematically by double arrow 34, may advantageously be coupled to rotate and/or translate the object containing tube 2 so as to present differing views of the object of interest 1. A pinhole aperture 127 is located at the focal point 128 of the convex lens and arranged to produce a cone beam of emergent radiation 125. As described above, a detector array 39 is located to receive the cone beam of emergent radiation 125 from the pinhole aperture 127. In one example embodiment, the outer tube 32A may advantageously have a port 38 and the space 33 around the object containing tube 2 is filled with a fluid such as optical oil having the same index of refraction as the outer tube 32A and the object containing tube 2.

Figure 4A:
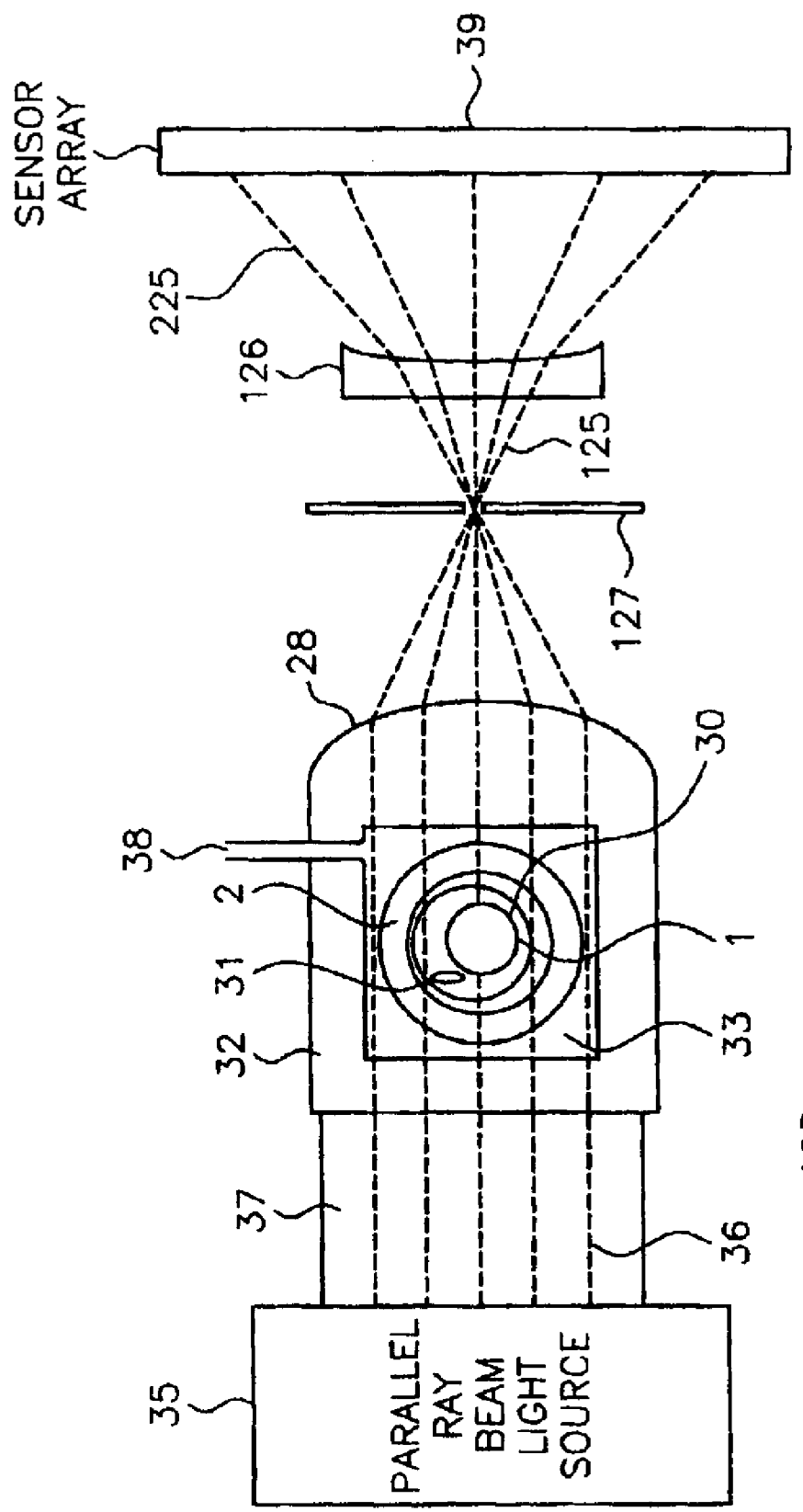
FIG. 4A schematically shows another example illustration of a system illumination geometry, including a single source-magnifying convex optic pair as contemplated by another alternate embodiment of the present invention.

Referring now to FIG. 4A, there shown schematically is another alternate embodiment of a system illumination geometry within a reconstruction cylinder 12D as contemplated by the present invention, where a cell or other object to be imaged 1 may be present in a flow tube or entrainment tube 2. The reconstruction cylinder 12D includes all of the elements as in the above embodiment described with respect to FIG. 4, with the addition of an optical element 126. The optical element 126 may advantageously comprise a plano-concave or other diverging or magnifying optic located between the pinhole aperture 127 and the sensor array 39. As in FIG. 4, a pinhole aperture 127 is located at the focal point 128 of the convex lens 28 and arranged to produce a cone beam of emergent radiation 125. The emergent radiation 125 is received by the plano-concave optical element 126, whereby it is further diverged into radiation beams 225. As described above, a detector array 39 is located to receive a cone beam of emergent radiation 225 from the pinhole aperture 127.

Figure 5:
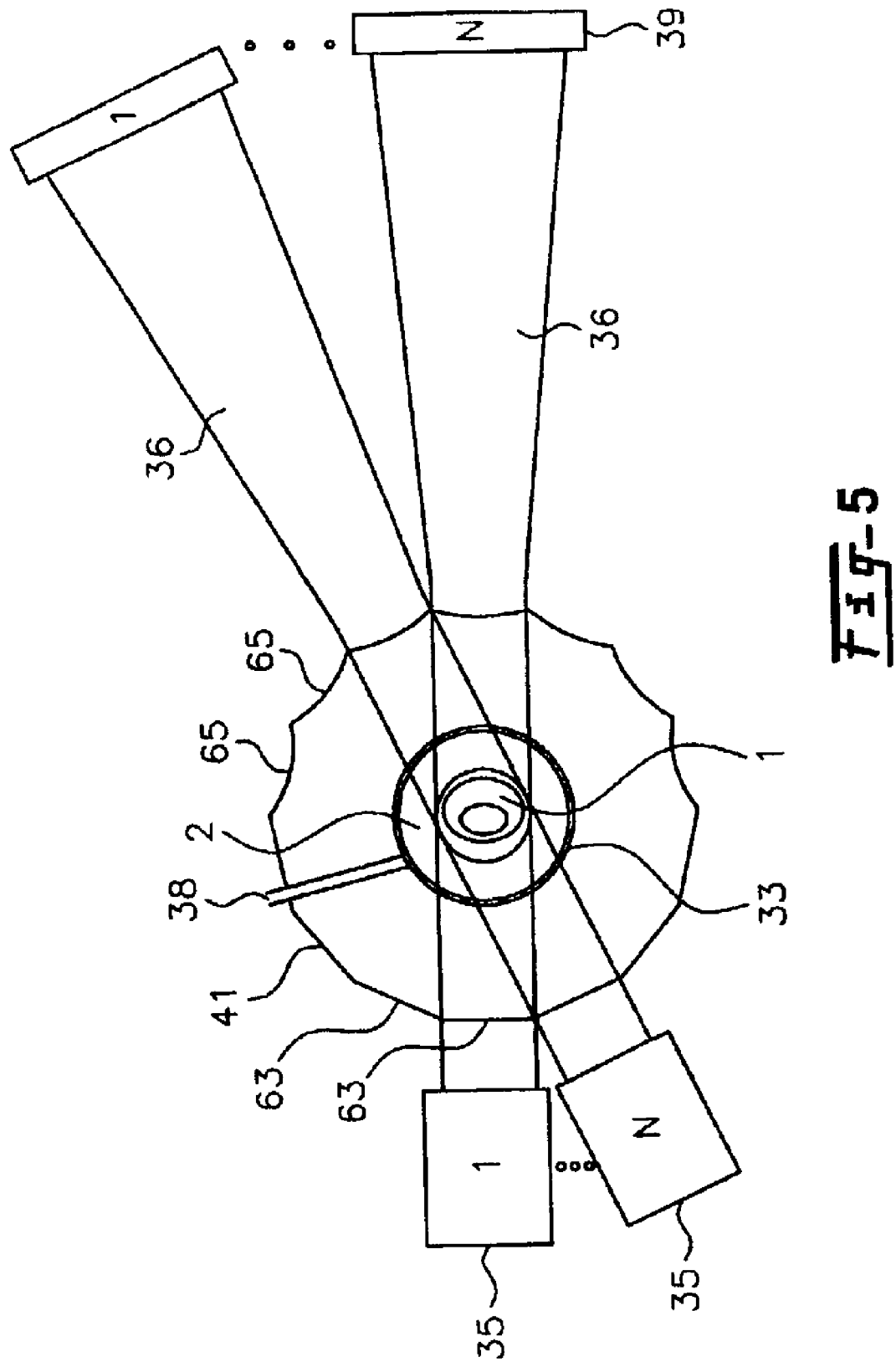
FIG. 5 schematically shows an example illustration of an illumination geometry and the imaged sample volume with multiple source-magnifying concave optic pairs as contemplated by an embodiment of the present invention.

FIG. 5 schematically shows an example illustration of illumination geometry and imaged sample volume with multiple source-magnifying concave optic pairs as contemplated by another embodiment of the present invention. A parallel-beam optical tomography system for imaging an object of interest 1 generally includes the illumination geometry described above with reference to FIG. 3 and a plurality of parallel ray beam radiation sources 1–N 35, where N is at least two, for illuminating the object of interest 1. Each of the plurality of parallel ray beam radiation sources 1–N 35 generates a plurality of parallel radiation beams at a differing angle of view with respect to the object of interest 1. Each of the plurality of parallel ray beam radiation sources 1–N 35 may be an individual light source, such as a laser, or at least one laser with light routed through one or more optical fibers or optical fiber bundles, as described herein below with respect to FIG. 8. An outer tube 41 has a plurality of optically flat input surfaces 63 and a plurality of corresponding concave output surfaces 65, where the plurality of corresponding concave output surfaces 65 cause the radiation emerging from the outer tube 41 to diverge after passing through the object of interest 1, so as to produce magnified projection images of the object 1. Alternatively, as described above with reference to FIG. 3, the post-specimen optic may comprise any magnifying optical element or combination of elements, including lens multiplets or other equivalents.

As in the other examples described herein, an object containing tube 2 is located within the outer tube 41, wherein the object of interest 1 is held within the object containing tube 2, and a plurality of detector arrays 1–N 39 are disposed to receive emerging radiation 36. Each of the plurality of detector arrays 1–N 39 is located to receive the emerging radiation 36 from one or more of the plurality of concave output surfaces 65.

Figure 5A:
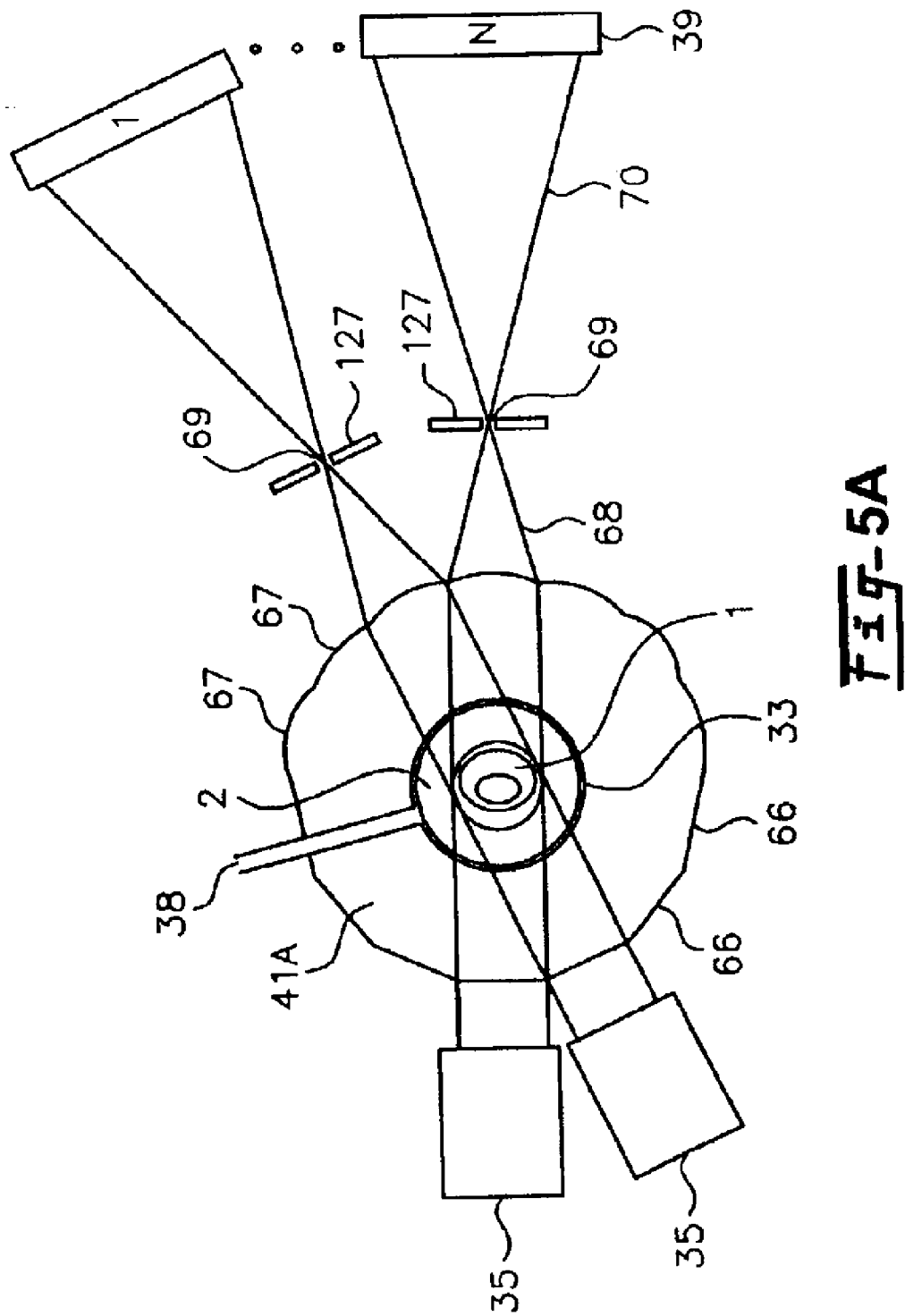
FIG. 5A schematically shows another example illustration of the illumination geometry and the imaged sample volume with multiple source-magnifying convex optic pairs as contemplated by an embodiment of the present invention.

FIG. 5A schematically shows another example illustration of illumination geometry and imaged sample volume with multiple source-magnifying convex optic pairs as contemplated by an embodiment of the present invention. FIG. 5A is constructed substantially similar to FIG. 5, with the exceptions that an outer tube 41A has a plurality of optically flat input surfaces 66 and a plurality of corresponding convex output surfaces 67, where the plurality of corresponding convex output surfaces 67 focus radiation 68 emerging from the outer tube 41A after passing through the object of interest 1. An object containing tube 2 is located within the outer tube 41A, wherein the object of interest 1 is held within the object containing tube 2. A plurality of pinhole apertures 127 are located at the respective focal points 69 of the convex output surfaces 67 where each of the plurality of pinhole apertures 127 receives radiation from one of the plurality of corresponding convex output surfaces 67 so as to produce an emergent cone beam 70.

A plurality of detector arrays 1–N 39 are disposed to receive the cone beams 70. Each of the plurality of detector arrays 1–N 39 is constructed as described hereinabove and located to receive the emerging radiation from one or more of the plurality of pinhole apertures 127.

Figure 6:
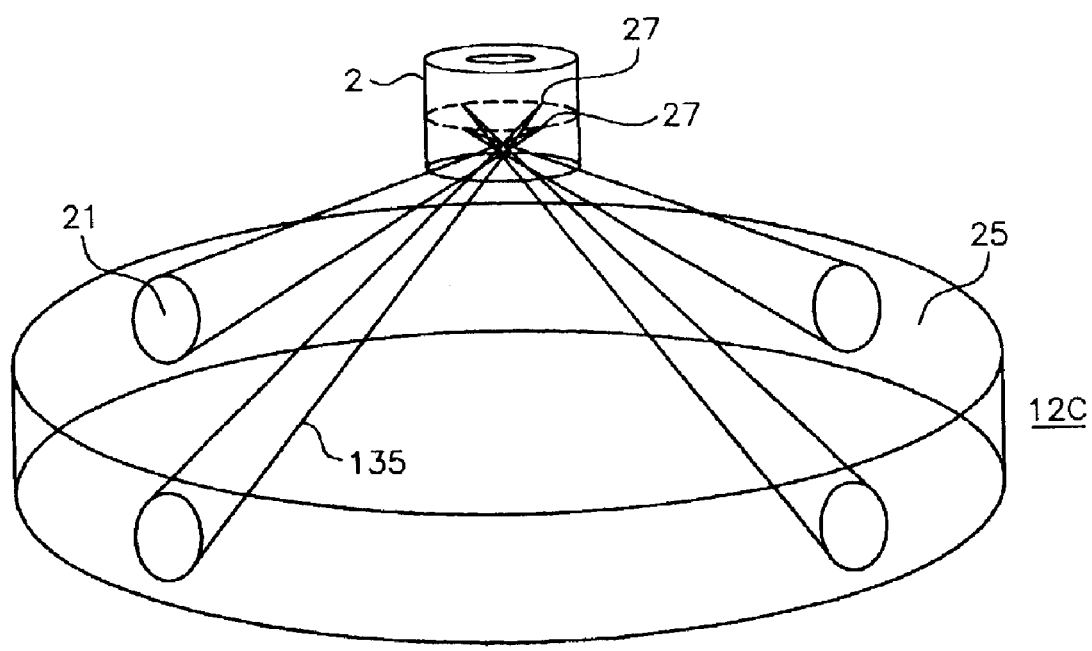
FIG. 6 is a highly schematic drawing that shows an example illustration of a reconstruction cylinder as contemplated by an embodiment of the present invention.

Referring to FIG. 6, there shown is a useful design of a reconstruction cylinder 12C as contemplated by an embodiment of this invention. Here, a ring of point sources 27 is disposed about the object containing tube 2 and a ring of image sensors 25 is placed in a plane situated above, at or below the plane containing the point sources 27. While only four point sources and four sensors are shown in the illustration, it will be understood that the rings of sources and image sensors may advantageously comprise a greater number, that being enough to enable tomographic reconstruction of imaged objects. The image sensors can be below or above or in the plane of the point sources. By placing the point sources 27 and image sensors 25 on separate planes, point sources on opposing sides of the cylinder will not physically interfere with other illumination beams. Each of the point sources may advantageously generate a parallel ray beam 135 which may be magnified after passing through the imaged object as described herein above with reference to FIGS. 3, 4, 4A, 5 and 5A.

During the course of moving through the reconstruction cylinder, the cell 1 passes through at least one photon point source. A central feature of the present invention is that a number of photon point sources 27 of selectable wavelength are disposed around and concentric with the object containing tube. The photon point sources operate in conjunction with opposing CCD, CMOS, TDI or other image sensors 25 that are sensitive to selectable portions of the light spectrum, thus allowing the acquisition of projections 21 of the light transmitted through the cell 1. In this manner, a set of projection rays 135 can be generated where the projection rays can be described as the straight line connecting the source point to an individual sensing element. The difference between the number of photons leaving the source point along a particular projection ray and the number of photons received at the particular sensing element is related to the number of photons lost or attenuated due to interactions with the cell and other contents of the object containing tube 2 along the projection ray path.

However, complications may arise from light scatter, photon energy shifts, imperfect geometry and poor collimation, and photons from different sources may arrive at a particular sensing element when multiple source points are energized simultaneously. With careful construction of the reconstruction cylinder, for example by judicious choice of the geometry for the pattern of point sources and their opposing detectors as described herein, and by proper timing or multiplexing of activation of the multiple point sources and readout of the sensor arrays, the photon contamination due to these issues can be minimized.

Photon contamination can be partially accounted for by calibration of the system, for example, with no cells present. That is, each light source may be illuminated in turn and its effects on each of the sensors can be measured, thereby providing offset data for use in normalizing the system. An additional calibration step may entail, for example, imaging latex polymer beads or other microspheres or oblate spheroids whose optical properties are known and span the density range of interest for cellular imaging.

Figure 7:
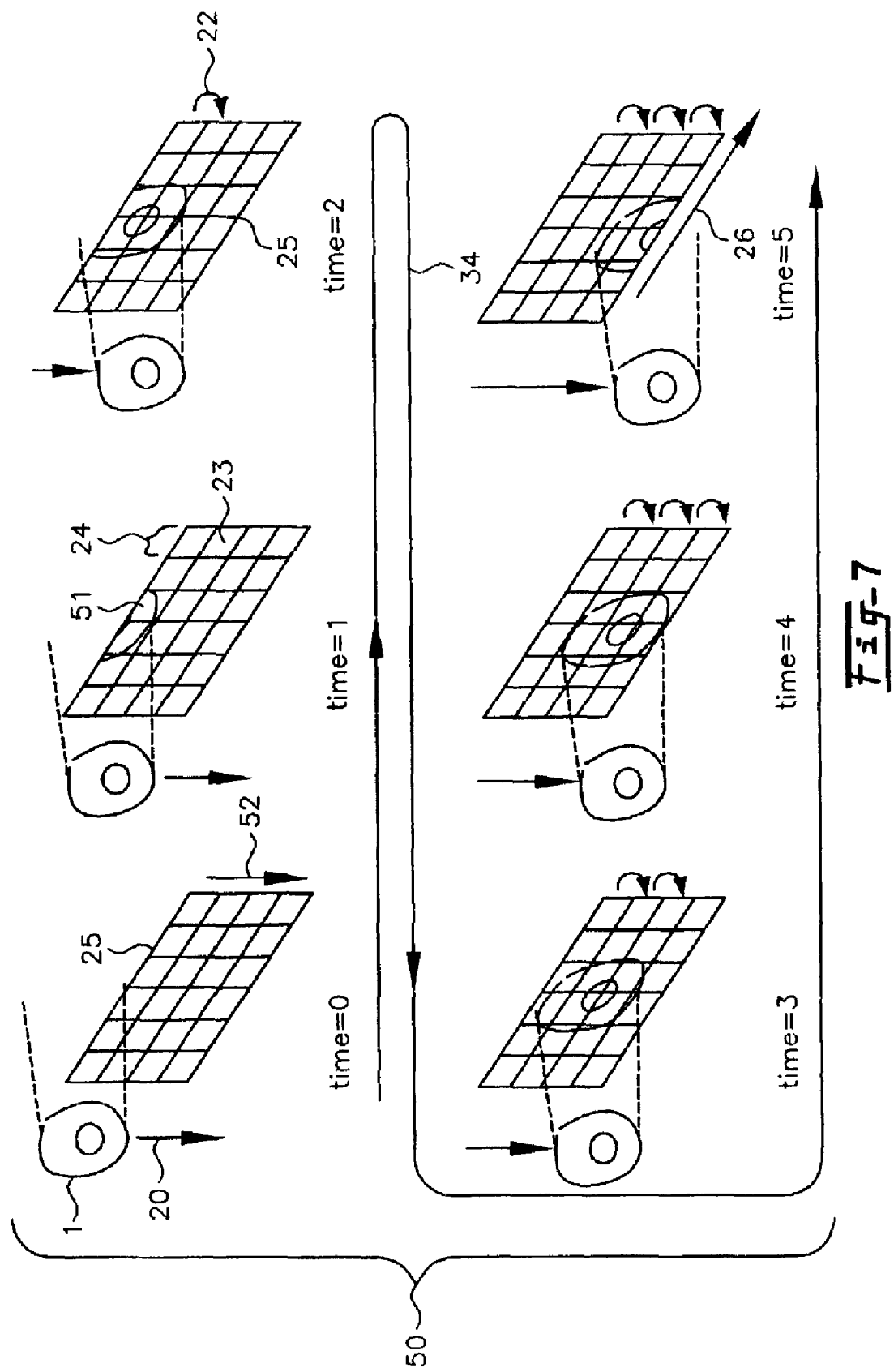
FIG. 7 schematically shows an example flow diagram illustrating the operation of a TDI image sensor as contemplated by an embodiment of the present invention.

Now referring to FIG. 7, there schematically shown is an example of a flow diagram 50 illustrating the operation of a TDI image sensor. Charge corresponding to an image element of the cell is transferred down a column of pixel elements 51 of the TDI sensor in synchrony with the image. The charge transfer occurs sequentially until the accumulated charge from the column is read out at the bottom register of the sensor 26.

In one embodiment of the optical tomography system contemplated by the invention, a plurality of TDI sensors 25 are oriented such that each sensor has a direction of line transfer 52 that is parallel to that of cell movement 20 along the z-axis. The TDI image sensor line transfer rate is synchronized to the velocity of the cells by timing or clocking signals from the computer 13.

The flow diagram of FIG. 7 shows a moving cell 1 and its location with respect to a TDI sensor 25 at various times along a time line 34. At time=0 the cell 1 is just above the TDI sensor 25 and no image is sensed. At time=1 the cell 1 is partially imaged by the TDI sensor 25. A shadowgram 51 of the cell 1 is imaged one line at a time. Electrical charges 22 corresponding to each image line are transferred to the next line of sensor pixel elements 23 in synchrony with the movement of that image line down the TDI image sensor from time=0 to time=5. In this way, electrical charge corresponding to each pixel is accumulated down each column 24 of the TDI detector 25 until it is read out at the bottom register 26 at time=5.

The TDI sensors are oriented such that the direction of line transfer 52 is the parallel to that of cell movement 20 along the z-axis. The TDI image sensor line transfer rate is synchronized to the velocity of the cells. Depending on the number of lines or stages in the TDI image sensor, additional photogenerated charge is accumulated and the signal is boosted (e.g. up to 96 fold with a 96 stage TDI sensor such as the Dalsa IL-E2 sensor).

Light Source.

Figure 8:
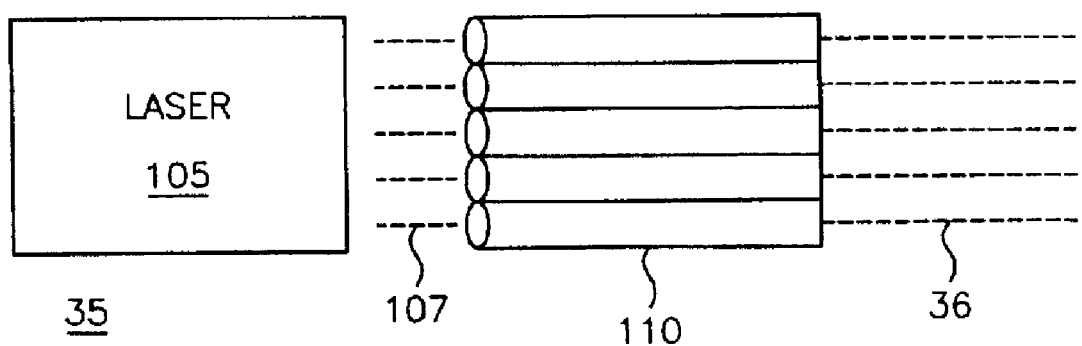
FIG. 8 schematically shows an example illustration of a parallel ray beam light source system as contemplated by an embodiment of the present invention.

Referring now to FIG. 8, an example illustration of a parallel ray beam light source as contemplated by an embodiment of the present invention is schematically shown. In this example, the parallel ray beam light source includes a laser 105 coupled to optical fibers 110. The optical fibers 110 may comprise individual fibers or optical fiber bundles or the equivalent. In operation the plurality of optical fibers 110 receive laser beams 107 and deliver parallel radiation beams 36 to source positions surrounding the flow tube or capillary tube. In this way, the number of lasers needed for multiple light source systems, such as, for example, described with respect to FIG. 5 and FIG. 5A above, may advantageously be reduced by routing light beams from a single laser through a number of optical fibers. Optical elements such as lenses and/or mirrors may be incorporated at the input or output, or both, of the optical fibers 110.

In operation, each laser beam diameter may be on the order of one-half to several millimeters, allowing a single laser to couple many optical fibers having openings ranging from about thirty microns to one hundred-micron fibers out of each laser source.

Each source may have the same general characteristics, preferably:

it may approximate a small circular point source, it may be a laser, laser diode or light emitting diode, it may be bright with known spectral content, the photons emitted from the source may form a beam of a known geometry such as a pencil beam where all photon rays are parallel.

Each source creates data for one projection angle. In an example data collection geometry, a plurality of sources arranged along a helix whose axis is the center axis of the object containing tube creates data from multiple projection angles as the cell moves through the module. Depending on the sensor geometry, several point sources could be disposed about the same circumference with angular separation such that the projections do not overlap at the sensor. The desired number of sources is a function of the needed resolution within each planar reconstruction (the x-y plane) or volumetric reconstruction. Further, the wavelength of the sources is selectable either by use of various diode or other lasers or by bandpass filtering of a white or other broadband source, for example a mercury or xenon arc lamp. There are several options that can be employed to create optical source points, such as:

a laser or laser diode, a laser-fiber bundle combination, an aperture in front of a laser or other high intensity photon source, an aperture utilizing surface plasmon focusing of photons on both the entry and exit sides of the pinhole, an optical fiber with a small cross-section, a virtual point source from a short focal length lens in front of a photon source, an electron beam that irradiates a point on a phosphor surface (a form of CRT), and various combinations of the above.

The geometry using a diverging beam of light is such that, the closer the point source to the object of interest 1 (e.g. a cell), the higher the magnification due to the wider geometric angle that is subtended by an object closer to the source. Magnification in a simple projection system is approximately $M=(A+B)/A$, where A is the distance between the point source and the object (cell) and B is the distance between the object and the detector. Conversely, if the required resolution is known in advance of the system design, then the geometry can be optimized for that particular resolution. For background, those skilled in the art are directed to Blass, M., editor-in-chief, *Handbook of Optics: Fiber Optics and Nonlinear Optics*, $2^{nd}$ ed., Vol. IV, Mcgraw-Hill, 2001.

Figure 9:
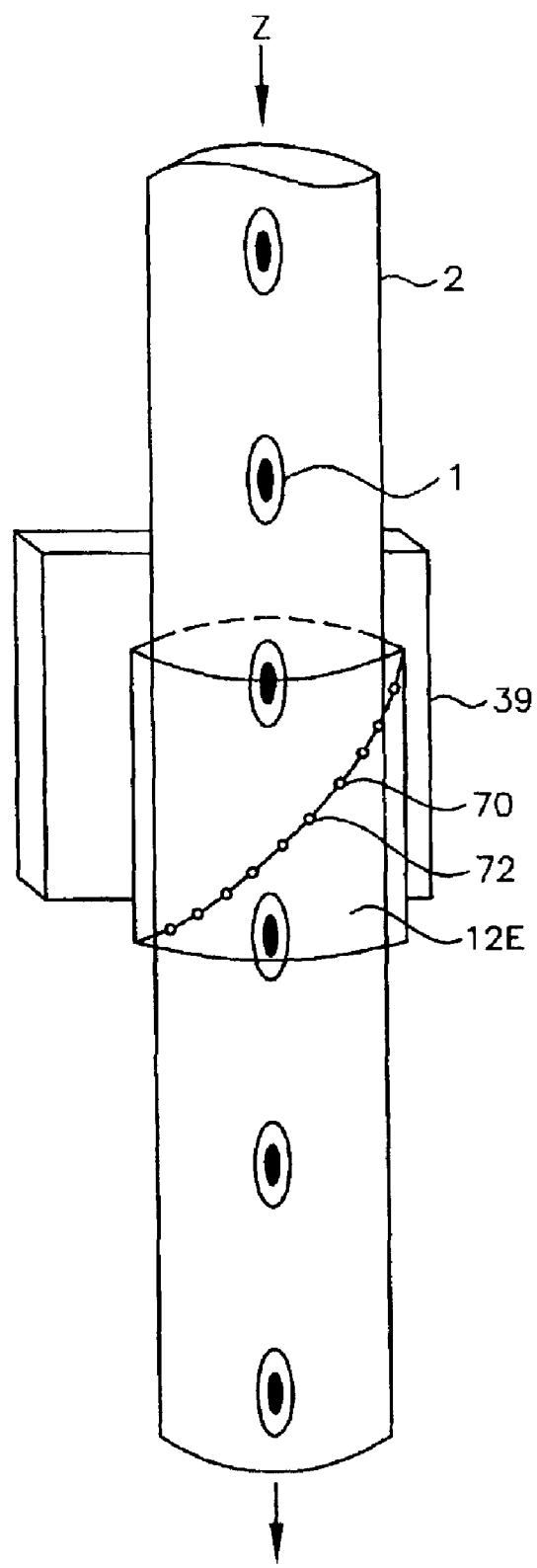
FIG. 9 schematically shows an example of a reconstruction cylinder surrounding a flow tube containing flowing object, such as cells, as contemplated by an embodiment of the present invention.

Referring now to FIG. 9, there shown schematically is an example of a reconstruction cylinder 12E, surrounding flow tube 2 containing flowing objects 1, such as cells, as contemplated by an embodiment of the present invention. A reconstruction cylinder 12E includes, for example, a helix 70 including a plurality of parallel ray beam sources 72 disposed at a predetermined helical pitch. Sensing elements 39 are disposed to receive light from the point sources, after it passes through the cell or other object of interest 1 and is magnified by post-specimen optical elements as described above with reference to FIGS. 3, 4, 4A, 5 and 5A.

While the arrangement of the plurality of parallel ray beam sources 72 is helical, an array of parallel ray beam sources used in a reconstruction cylinder as contemplated by the present invention may take on a wide variety of geometric patterns, depending in part on the speed of the electronics, the cell velocity and the geometry that achieves non-overlapping projection signals at the sensor (detector).

Figure 10:
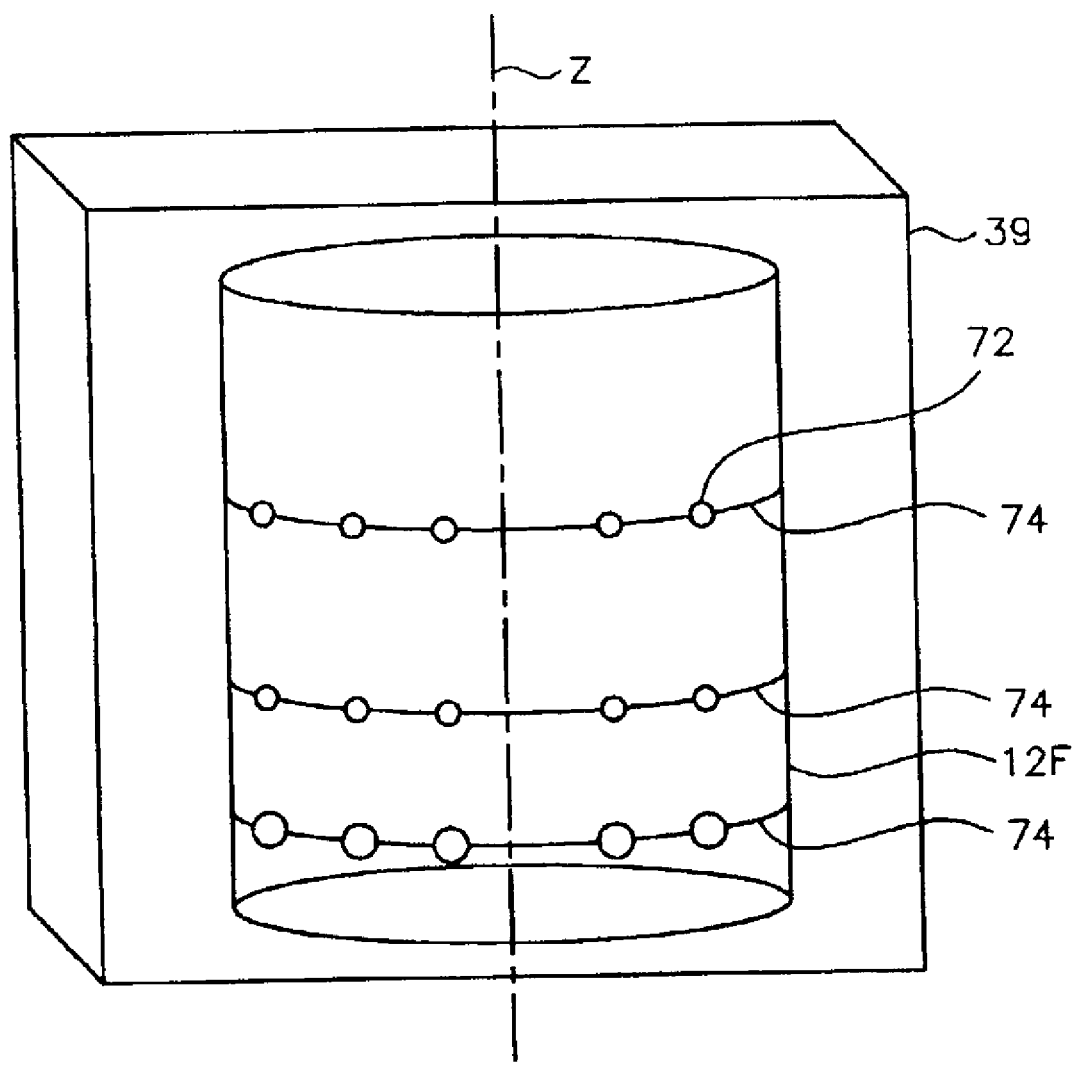
FIG. 10 schematically shows an example of a reconstruction cylinder including a series of partial circumferences arranged along a Z-axis through an object containing tube, wherein each partial circumference may contain more than one source-detector pair.

For example, with reference to FIG. 10, there shown is a reconstruction cylinder 12F including a series of partial circumferences 74 arranged along a Z-axis through the object containing tube 2, wherein each partial circumference 74 may contain more than one source-detector pair.

The fixed optical point sources 72, in conjunction with opposing detectors 39 mounted around a circumference of the tube can sample multiple projection angles through the entire cell as it flows past the sources. By timing of the emission or readout, or both, of the light source and attenuated transmitted and/or scattered and/or emitted light, each detected signal will coincide with a specific, known position along the axis in the z-direction of the flowing cell. In this manner, a cell flowing with known velocity along a known axis perpendicular to a light source that is caused to emit or be detected in a synchronized fashion can be optically sectioned with projections through the cell that can be reconstructed to form a 2D slice in the x-y plane. By stacking or mathematically combining sequential slices, a 3D picture of the cell will emerge. It is also possible to combine the cell motion with the positioning of the light source (or sources) around the flow axis to generate data that can be reconstructed, for example, in a helical manner to create a 3D picture of the cell. Three dimensional reconstruction can be done either by stacking contiguous planar images reconstructed from linear (1D) projections, or from planar (2D) projections directly. The 3D picture of the cell can yield quantitative measures of sub-cellular structures and the location and amount of tagged molecular probes that provide diagnostic information.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A parallel-beam optical tomography system for imaging an object of interest comprising:
   a plurality of parallel beam radiation sources for illuminating the object of interest with a plurality of parallel radiation beams; and
   an object containing tube, wherein the object of interest is held within the object containing tube, and wherein the object containing tube has a reconstruction cylinder positioned around the object containing tube, wherein the reconstruction cylinder holds the plurality of parallel beam radiation sources in a geometrical arrangement around a circumference of a sample including the object of interest, and wherein the reconstruction cylinder further includes a detector array located to receive emerging radiation from the illuminated object of interest.

2. The parallel-beam optical tomography system of claim 1 wherein the object of interest comprises a cell.

3. The parallel-beam optical tomography system of claim 1 wherein at least one of the plurality of parallel beam radiation sources comprises a laser.

4. The parallel-beam optical tomography system of claim 3 wherein the laser emits radiation in the visible portion of the electromagnetic spectrum.

5. The parallel-beam optical tomography system of claim 3 wherein the laser emits radiation in the ultraviolet portion of the electromagnetic spectrum.

6. The parallel-beam optical tomography system of claim 1 wherein the object of interest includes a molecular probe.

7. The parallel-beam optical tomography system of claim 1 wherein the detector array comprises a detector array selected from the group consisting of solid state sensors, charge coupled device sensors, complementary metal oxide semiconductor sensors and time delay and integration sensors.

8. The parallel-beam optical tomography system of claim 1 wherein the object containing tube is coupled to a mechanical stage or micromanipulator that rotates the object containing tube to present differing views of the object of interest.

9. The parallel-beam optical tomography system of claim 1 wherein the object containing tube is within an outer tube having an optically flat input surface and a concave output surface or plano-concave lens, where the concave outer surface or plano-concave lens diverges radiation emerging from the outer tube after passing through the object of interest.

10. The parallel-beam optical tomography system of claim 9 wherein the outer tube further comprises a space around the object containing tube in communication with a port for filling the space around the object containing tube with optical oil having the same index of refraction as the outer tube and the object containing tube.

11. The parallel-beam optical tomography system of claim 1 wherein the parallel ray beam radiation source is selected from the group consisting of a laser,
   a laser-fiber bundle combination,
   an aperture in front of a laser or other high intensity photon source,
   an aperture utilizing surface plasmon focusing of photons on both the entry and exit sides of the pinhole,
   an optical fiber with a small cross-section,
   a virtual point source from a short focal length lens in front of a photon source, and
   an electron beam that irradiates a point on a phosphor surface, and combinations of the aforesaid elements.

12. The parallel-beam optical tomography system of claim 1 wherein the object containing tube comprises a flow tube.

13. The parallel-beam optical tomography system of claim 12, wherein the object of interest has a flow velocity, and wherein the geometrical arrangement comprises an arrangement from the group consisting of a series of partial circumferences arranged along the z-axis wherein each partial circumference includes at least one source-detector pair, and a helix having a pitch that is a function of the flow velocity.

14. A parallel-beam optical tomography system for imaging an object of interest comprising:
   a parallel beam radiation source for illuminating the object of interest with a plurality of parallel radiation beams;
   an outer tube having an optically flat input surface and a convex output surface or convex lens, where the convex output surface or convex lens focuses radiation emerging from the outer tube after passing through the object of interest;
   an object containing tube located within the outer tube, wherein the object of interest is held within the object containing tube;
   a mechanical stage or micromanipulator coupled to rotate the object containing tube to present differing views of the object of interest;
   a pinhole aperture located at the focal point of the convex lens and arranged to produce a cone beam of emergent radiation; and
   a detector array located to receive the cone beam of emergent radiation from the pinhole aperture.

15. The parallel-beam optical tomography system of claim 14 wherein the object of interest comprises a cell.

16. The parallel-beam optical tomography system of claim 14 wherein the parallel beam radiation source comprises a laser.

17. The parallel-beam optical tomography system of claim 14 wherein the laser emits radiation in the visible portion of the electromagnetic spectrum.

18. The parallel-beam optical tomography system of claim 14 wherein the laser emits radiation in the ultraviolet portion of the electromagnetic spectrum.

19. The parallel-beam optical tomography system of claim 14 wherein the outer tube further comprises a port and space around the object containing tube filled with optical oil having the same index of refraction as the outer tube and object containing tube.

20. The parallel-beam optical tomography system of claim 14 wherein the object of interest includes a molecular probe.

21. The parallel-beam optical tomography system of claim 14 wherein the detector array comprises a detector array selected from the group consisting of solid state sensors, charge coupled device sensors, complementary metal oxide semiconductor sensors and time delay and integration sensors.

22. The parallel-beam optical tomography system of claim 14 further comprising a plano-concave lens, or other diverging or magnifying optic located between the pinhole aperture and the detector array.

23. The parallel-beam optical tomography system of claim 14 wherein the object containing tube comprises a flow tube and a reconstruction cylinder is positioned around the object containing tube, wherein the reconstruction cylinder incorporates the pinhole aperture and a plurality of additional pinhole apertures in a geometrical arrangement around a circumference of a sample including the object of interest for illuminating the object of interest and the reconstruction cylinder further includes the detector array and a plurality of additional detector arrays located to receive emissions from the illuminated object of interest.

24. A parallel-beam optical tomography system for imaging an object of interest comprising:
a plurality of parallel beam radiation sources for illuminating the object of interest, each of the plurality of parallel beam radiation sources generating a plurality of parallel radiation paths at a differing angle of view with respect to the object of interest;
an outer tube having a plurality of optically flat input surfaces and a plurality of corresponding concave output surfaces or concave lenses, where the plurality of corresponding concave output surfaces or concave lenses diverge radiation emerging from the outer tube after passing through the object of interest;
an object containing tube located within the outer tube, wherein the object of interest is held within the object containing tube; and
a plurality of detector arrays, where each of the plurality of detector arrays is located to receive the emerging radiation from one or more of the plurality of concave output surfaces.

25. The parallel-beam optical tomography system of claim 24 wherein the object containing tube incorporates a mechanism for movement of the object containing tube.

26. The parallel-beam optical tomography system of claim 24 wherein the object of interest comprises a cell.

27. The parallel-beam optical tomography system of claim 24 wherein the plurality of parallel beam radiation sources comprises a plurality of lasers.

28. The parallel-beam optical tomography system of claim 27 wherein the plurality of lasers emits radiation in the visible portion of the electromagnetic spectrum.

29. The parallel-beam optical tomography system of claim 27 wherein the plurality of lasers emits radiation in the ultraviolet portion of the electromagnetic spectrum.

30. The parallel-beam optical tomography system of claim 27 wherein the outer tube further comprises a port and space around the object containing tube is filled with optical oil having the same index of refraction as the outer tube and object containing tube.

31. The parallel-beam optical tomography system of claim 24 wherein the object of interest includes a molecular probe.

32. The parallel-beam optical tomography system of claim 24 wherein the plurality of detector arrays comprises a detector array selected from the group consisting of solid state sensors, charge coupled device sensors, complementary metal oxide semiconductor sensors and time delay and integration sensors.

33. The parallel-beam optical tomography system of claim 24 wherein the plurality of parallel beam radiation sources comprises a plurality of optical fibers or fiber bundles coupled to at least one laser.

34. The parallel-beam optical tomography system of claim 24 wherein the object containing tube comprises a flow tube and a reconstruction cylinder is positioned around the object containing tube, wherein the reconstruction cylinder holds the plurality of parallel beam radiation sources in a geometrical arrangement around a circumference of a sample including the object of interest for illuminating the object of interest and the reconstruction cylinder further holds the plurality of detector arrays.

35. The parallel-bear optical tomography system of claim 34 wherein the object of interest has a flow velocity, and wherein the geometrical arrangement comprises an arrangement from the group consisting of a series of partial circumferences arranged along the z-axis wherein each partial circumference includes at least one source-detector pair, and a helix having a pitch that is a function of the flow velocity.

36. A parallel-beam optical tomography system for imaging an object of interest comprising:
a plurality of parallel beam radiation sources for illuminating the object of interest, each of the plurality of parallel beam radiation sources generating a plurality of parallel radiation paths at a differing angle of view of the object of interest;
an outer tube having a plurality of optically flat input surfaces and a plurality of corresponding convex output surfaces or convex lenses, where the plurality of corresponding convex output surfaces or convex lenses focus radiation emerging from the outer tube after passing through the object of interest;
an object containing tube located within the outer tube, wherein the object of interest is held within the object containing tube;
a plurality of pinhole apertures, where each of the plurality of pinhole apertures receives radiation from one of the plurality of corresponding convex output surfaces or lenses so as to produce an emergent cone beam; and
a plurality of detector arrays, where each of the plurality of detector arrays is located to receive the emerging radiation from one of the plurality of pinhole apertures.

37. The parallel-beam optical tomography system of claim 36 that may incorporate a mechanism for movement of the tube.

38. The parallel-beam optical tomography system of claim 36 wherein the object of interest comprises a cell.

39. The parallel-beam optical tomography system of claim 36 wherein the plurality of parallel beam radiation sources comprises a plurality of lasers.

40. The parallel-beam optical tomography system of claim 39 wherein the plurality of lasers emits radiation in the visible portion of the electromagnetic spectrum.

41. The parallel-beam optical tomography system of claim 39 wherein the plurality of lasers emits radiation in the ultraviolet portion of the electromagnetic spectrum.

42. The parallel-beam optical tomography system of claim 36 wherein the plurality of parallel beam radiation sources comprises a plurality of optical fibers or fiber bundles coupled to at least one laser.

43. The parallel-beam optical tomography system of claim 36 wherein the outer tube further comprises a port and space around the object containing tube is filled with optical oil having the same index of refraction as the outer and object containing tubes.

44. The parallel-beam optical tomography system of claim 36 wherein the object of interest includes a probe.

45. The parallel-beam optical tomography system of claim 36 wherein the plurality of detector arrays comprise a detector array selected from the group consisting of solid state sensors, charge coupled device sensors, complementary metal oxide semiconductor sensors and time delay and integration sensors.

46. The parallel-beam optical tomography system of claim 36 further comprising a plurality of optical elements between the plurality of pinhole apertures and the plurality of detector sensor arrays.

47. The parallel-beam optical tomography system of claim 46 wherein the plurality of optical elements are selected from the group consisting of plano-concave lenses, magnifying optical elements and diverging optical elements.

48. The method of claim 46 wherein the reconstruction cylinder has more than one plane of point sources with the associated planes of sensors where each plane of sources and associated sensors are radially offset from the previous to capture different perspectives.

49. The parallel-beam optical tomography system of claim 36 wherein the object containing tube comprises a flow tube and a reconstruction cylinder is positioned around the object containing tube, wherein the reconstruction cylinder holds the plurality of pinhole apertures and the plurality of detector arrays.

50. The parallel-beam optical tomography system of claim 49, wherein the object of interest has a flow velocity, and wherein the geometrical arrangement comprises an arrangement from the group consisting of a series of partial circumferences arranged along the z-axis wherein each partial circumference includes at least one pinhole aperture-detector pair, and a helix having a pitch that is a function of the flow velocity.

51. A method for three dimensional reconstruction of an object of interest comprising the steps of:

packing at least one object of interest into a linear container;

moving the linear container at a rate of translation;

illuminating the at least one object of interest with at least one parallel beam radiation source; and generating at least one projection image with a time delay and integration (TDI) image sensor having a line transfer rate synchronized to the rate of translation.

52. The method of claim 51 wherein the at least one object of interest is a cell or a cell nucleus.

53. A method for three dimensional reconstruction of an object of interest using a reconstruction cylinder design wherein a plane of point sources and a plane of sensors are parallel and concentric, one above the other, and wherein the reconstruction cylinder has an arrangement of sources and detectors around a circumference of a sample, the method comprising the steps of:

(a) injecting objects of interest into a flow stream of controlled velocity;

(b) illuminating the object of interest with a plurality of parallel optical projection beams; and (c) generating a set of projection images at a plurality of angles for each object as it flows through the reconstruction cylinder.

54. A method for three dimensional reconstruction of an object of interest using a reconstruction cylinder including at least one plane of point sources and at least one plane of sensors that are parallel and concentric to the at least one plane of point sources, one above the other, and arranged around a circumference of a sample in a linear container including at least one object of interest, the method comprising the steps of:

(a) packing the at least one object of interest into a linear container;

(b) illuminating the at least one object of interest with a plurality of parallel optical projection beams;

(c) translating the linear container until a selected object of interest is located within a region of the plurality of optical projection beams;

(d) centering the selected object of interest as necessary;

(e) generating a set of projection images from the selected object of interest at a plurality of angles; and (f) repeating the steps (b) through (e) until the selected object of interest has been scanned.

55. The method of claim 54 wherein the reconstruction cylinder has more than one plane of point sources with the associated planes of sensors where each plane of point sources and associated sensors are radially offset from each other to capture different perspectives.

56. The method of claim 54 wherein the step of generating a set of projection images at a plurality of angles further comprises the step of selecting individual transaxial images through the imaged object as reconstructed from a subset of the data acquired by the sensor arrays.

* * * * *